United States Patent [19]
Larsen et al.

[11] Patent Number: 5,993,459
[45] Date of Patent: Nov. 30, 1999

[54] SUTURE ANCHOR INSTALLATION SYSTEM WITH INSERTION TOOL

[76] Inventors: Scott Larsen, 18 Sugar Hill Rd., Newtown, Conn. 06470; Daniel R. Lee, 15 Devonshire La., Madison, Conn. 06443

[21] Appl. No.: 09/176,829

[22] Filed: Oct. 22, 1998

Related U.S. Application Data

[63] Continuation of application No. 08/919,902, Aug. 28, 1997, abandoned, which is a continuation of application No. 08/726,026, Oct. 4, 1996, abandoned.

[51] Int. Cl.$^6$ .................................................. A61B 17/04
[52] U.S. Cl. ........................................ 606/104; 606/104
[58] Field of Search .................................. 606/139, 104, 606/232

[56] References Cited

U.S. PATENT DOCUMENTS

| | | |
|---|---|---|
| 2,121,193 | 6/1938 | Hanicke . |
| 2,381,050 | 8/1945 | Hardinge . |
| 2,489,870 | 11/1949 | Dzus . |
| 2,490,364 | 12/1949 | Livingston . |
| 2,579,438 | 12/1951 | Longfellow . |
| 2,699,774 | 1/1955 | Livingston . |
| 3,759,257 | 9/1973 | Fischer et al. . |
| 3,760,802 | 9/1973 | Fischer et al. . |
| 3,768,635 | 10/1973 | Eggert . |

(List continued on next page.)

FOREIGN PATENT DOCUMENTS

| | | |
|---|---|---|
| 0019782 | 12/1980 | European Pat. Off. . |
| 075330 | 3/1983 | European Pat. Off. . |
| 0077868 | 5/1983 | European Pat. Off. . |

(List continued on next page.)

OTHER PUBLICATIONS

Raftopoulos, "A Proposed Design For An Expanding Hip Nail," Engineering in Medicine, vol. 11 (1982), pp. 187–188.

Design News, "Ligament Fastener Cuts Recovery Time," pp. 56–57, (1989).
Instrument Makar Inc., "The Ligamentous and Capsular Repair System", Arthroscopy Equipment and Supplies, Section One, p. 4.
Biomet Inc., "Ligament Screw System," 1990.
Arthrex, "The Complete Arthrex Information System."
Mitek Surgical Products, "Mitek GII Anchor, High Strength Fixation," 1991.
Mitek Surgical Products, "Mitek Anchor System, Effective Soft Tissue Reattachment," 1990.
Mitek Surgical Products, Mitek Quick Anchor, "Fast, Effective, Soft Tissue Reattachment," 1990.
Zimmer, Inc., "Statak® Soft Tissue Attachment Device," 1988.
Acufex Microsurgical Inc., "TAG® Tissue Anchor Guide System."
Acufex Microsurgical Inc., "Technique for Using the TAG® Tissue Anchor—Rod Style."
Acufex Microsurgical Inc., "Technique for Using the TAG® Tissue Anchor—Wedge Style."
Assembly Engineering, "Special Blind Rivets," 1979.
K. Hoffer, Bremen, Rivet Joints in Aluminum Structural Components (1), vol. 59, 1983.

*Primary Examiner*—Gary Jackson

[57] ABSTRACT

A suture anchor installation system includes a suture anchor, a loading unit, and a suture anchor installation tool. The suture anchor includes an elongated setting pin at least partially mounted within a longitudinal bore of a socket and slidably movable between a distal first position wherein at least a portion of the setting pin is distal to the socket and a proximal second position, the socket having at least two proximally pointing legs which are radially expandable in response to movement of the setting pin to the proximal second position. The loading unit includes a housing and a collet movably mounted within an axial bore in the housing, the collet having arms for releasably gripping the suture anchor. The suture anchor inserter has a first tubular member for engaging the collet, and a second tubular member for releasably engaging the socket of the suture anchor.

21 Claims, 19 Drawing Sheets

U.S. PATENT DOCUMENTS

| | | |
|---|---|---|
| 3,779,239 | 12/1973 | Fischer et al. . |
| 3,782,374 | 1/1974 | Fischer . |
| 3,805,775 | 4/1974 | Fischer et al. . |
| 3,846,846 | 11/1974 | Fischer . |
| 3,910,281 | 10/1975 | Kletschka et al. . |
| 3,951,261 | 4/1976 | Mandel et al. . |
| 3,958,488 | 5/1976 | Fischer . |
| 3,986,504 | 10/1976 | Avila . |
| 4,006,747 | 2/1977 | Kronenthal et al. . |
| 4,013,071 | 3/1977 | Rosenberg . |
| 4,091,806 | 5/1978 | Aginsky . |
| 4,135,623 | 1/1979 | Thyen . |
| 4,204,531 | 5/1980 | Aginsky . |
| 4,227,518 | 10/1980 | Aginsky . |
| 4,236,512 | 12/1980 | Aginsky . |
| 4,244,370 | 1/1981 | Furlow et al. . |
| 4,259,072 | 3/1981 | Hirabayashi et al. . |
| 4,262,665 | 4/1981 | Roalstad et al. . |
| 4,275,717 | 6/1981 | Bolesky . |
| 4,309,137 | 1/1982 | Tanaka et al. . |
| 4,339,217 | 7/1982 | Lacey . |
| 4,351,069 | 9/1982 | Ballintyn et al. . |
| 4,409,974 | 10/1983 | Freedland . |
| 4,414,967 | 11/1983 | Shapiro . |
| 4,424,898 | 1/1984 | Thyen et al. . |
| 4,453,539 | 6/1984 | Raftopoulos et al. . |
| 4,454,875 | 6/1984 | Pratt et al. . |
| 4,456,005 | 6/1984 | Lichty . |
| 4,474,517 | 10/1984 | Navoczynski . |
| 4,483,678 | 11/1984 | Nishio et al. . |
| 4,519,100 | 5/1985 | Wills et al. . |
| 4,519,735 | 5/1985 | Mächtle . |
| 4,520,511 | 6/1985 | Gianezio et al. . |
| 4,539,981 | 9/1985 | Tunc . |
| 4,542,539 | 9/1985 | Rowe, Jr. et al. . |
| 4,550,448 | 11/1985 | Kenna ........................ 623/16 |
| 4,550,449 | 11/1985 | Tunc . |
| 4,570,623 | 2/1986 | Ellison et al. . |
| 4,586,502 | 5/1986 | Bedi et al. . |
| 4,590,928 | 5/1986 | Hunt et al. . |
| 4,590,930 | 5/1986 | Kurth et al. . |
| 4,591,048 | 5/1986 | Eldridge, Jr. . |
| 4,596,503 | 6/1986 | Mirsberger et al. ............. 411/32 |
| 4,599,085 | 7/1986 | Riess et al. ................ 623/16 |
| 4,612,923 | 9/1986 | Kronenthal . |
| 4,621,640 | 11/1986 | Mulhollan et al. . |
| 4,632,100 | 12/1986 | Somers et al. . |
| 4,637,765 | 1/1987 | Omata . |
| 4,640,271 | 2/1987 | Lower . |
| 4,653,486 | 3/1987 | Coker . |
| 4,655,777 | 4/1987 | Dunn et al. . |
| 4,656,806 | 4/1987 | Leibhard et al. . |
| 4,669,473 | 6/1987 | Richards et al. . |
| 4,681,590 | 7/1987 | Tansey ........................ 623/23 |
| 4,699,271 | 10/1987 | Lincoln et al. . |
| 4,711,232 | 12/1987 | Fischer et al. . |
| 4,713,076 | 12/1987 | Draenert . |
| 4,716,893 | 1/1988 | Fischer et al. . |
| 4,738,255 | 4/1988 | Goble et al. . |
| 4,741,330 | 5/1988 | Hayhurst . |
| 4,759,670 | 7/1988 | Linder et al. .................. 411/43 |
| 4,760,843 | 8/1988 | Fischer et al. . |
| 4,767,248 | 8/1988 | Pratt . |
| 4,776,328 | 10/1988 | Frey et al. . |
| 4,776,329 | 10/1988 | Treharne . |
| 4,778,468 | 10/1988 | Hunt et al. . |
| 4,787,378 | 11/1988 | Sodhi . |
| 4,790,303 | 12/1988 | Steffee .................... 128/924 M |
| 4,790,304 | 12/1988 | Rosenberg . |
| 4,793,335 | 12/1988 | Frey et al. . |
| 4,796,612 | 1/1989 | Reese . |
| 4,806,053 | 2/1989 | Herb . |
| 4,818,163 | 4/1989 | Bereiter et al. . |
| 4,828,562 | 5/1989 | Kenna . |
| 4,834,752 | 5/1989 | Van Kampen . |
| 4,861,197 | 8/1989 | Calandra, Jr. . |
| 4,870,957 | 10/1989 | Goble et al. . |
| 4,871,289 | 10/1989 | Choiniere . |
| 4,895,148 | 1/1990 | Bays et al. . |
| 4,898,156 | 2/1990 | Gatturna et al. . |
| 4,898,505 | 2/1990 | Froehlich . |
| 4,899,743 | 2/1990 | Nicholson et al. . |
| 4,921,383 | 5/1990 | Fischer . |
| 4,927,421 | 5/1990 | Goble et al. . |
| 4,938,760 | 7/1990 | Burton et al. ..................... 600/29 |
| 4,946,468 | 8/1990 | Li . |
| 4,963,144 | 10/1990 | Huene . |
| 4,968,315 | 11/1990 | Gatturna . |
| 4,969,887 | 11/1990 | Sodhi ........................ 606/67 |
| 4,969,892 | 11/1990 | Burton et al. . |
| 4,976,680 | 12/1990 | Hayman et al. . |
| 4,976,715 | 12/1990 | Bays et al. . |
| 4,988,351 | 1/1991 | Paulos et al. . |
| 5,002,550 | 3/1991 | Li . |
| 5,011,473 | 4/1991 | Gatturna . |
| 5,013,316 | 5/1991 | Goble et al. . |
| 5,015,250 | 5/1991 | Foster ........................ 606/147 |
| 5,036,862 | 8/1991 | Pohndorf ..................... 128/784 |
| 5,037,422 | 8/1991 | Hayburst . |
| 5,041,129 | 8/1991 | Hayburst et al. . |
| 5,046,513 | 9/1991 | Gatturna et al. . |
| 5,053,047 | 10/1991 | Yoon . |
| 5,071,420 | 12/1991 | Paulos et al. . |
| 5,076,746 | 12/1991 | Fischer et al. . |
| 5,078,730 | 1/1992 | Li et al. . |
| 5,080,543 | 1/1992 | Murphy . |
| 5,084,050 | 1/1992 | Draenert . |
| 5,085,545 | 2/1992 | Takahashi . |
| 5,085,661 | 2/1992 | Moss . |
| 5,100,405 | 3/1992 | McLaren ..................... 606/72 |
| 5,100,417 | 3/1992 | Cerier et al. . |
| 5,102,421 | 4/1992 | Anspach, Jr. . |
| 5,122,133 | 6/1992 | Evans . |
| 5,129,906 | 7/1992 | Ross et al. ................... 606/77 |
| 5,131,533 | 7/1992 | Alpern . |
| 5,144,961 | 9/1992 | Chen et al. . |
| 5,154,719 | 10/1992 | Cotrel ........................ 606/73 |
| 5,156,616 | 10/1992 | Meadows et al. . |
| 5,167,664 | 12/1992 | Hodorek . |
| 5,167,665 | 12/1992 | McKinney . |
| 5,176,682 | 1/1993 | Chow . |
| 5,203,784 | 4/1993 | Ross et al. . |
| 5,207,679 | 5/1993 | Li . |
| 5,209,753 | 5/1993 | Biedermann et al. . |
| 5,217,486 | 6/1993 | Rice et al. . |
| 5,224,946 | 7/1993 | Hayhurst et al. ............. 606/72 |
| 5,236,445 | 8/1993 | Hayhurst et al. . |
| 5,246,441 | 9/1993 | Ross et al. . |
| 5,258,016 | 11/1993 | DiPoto et al. . |
| 5,268,001 | 12/1993 | Nicholson et al. . |
| 5,336,240 | 8/1994 | Metzler et al. . |
| 5,354,298 | 10/1994 | Lee et al. . |
| 5,423,860 | 6/1995 | Lizardi et al. ............... 606/232 |
| 5,441,502 | 8/1995 | Bartlett . |
| 5,480,403 | 1/1996 | Lee et al. .................... 606/72 |
| 5,522,844 | 6/1996 | Johnson . |
| 5,531,699 | 7/1996 | Tomba et al. . |
| 5,534,011 | 7/1996 | Greene, Jr. et al. . |
| 5,584,860 | 12/1996 | Goble et al. . |
| 5,628,751 | 5/1997 | Sander et al. ............... 606/104 |
| 5,643,320 | 7/1997 | Lower et al. . |
| 5,662,658 | 9/1997 | Wenstrom, Jr. . |
| 5,667,513 | 9/1997 | Torrie et al. . |
| 5,741,268 | 4/1998 | Schutz . |

FOREIGN PATENT DOCUMENTS

| | | |
|---|---|---|
| 0 124 489 | 11/1984 | European Pat. Off. . |
| 0232049 | 1/1987 | European Pat. Off. . |
| 0 232 049 | 8/1987 | European Pat. Off. . |
| 0230937 | 8/1987 | European Pat. Off. . |

| | | |
|---|---|---|
| 0238223 | 9/1987 | European Pat. Off. . |
| 0241240 | 10/1987 | European Pat. Off. . |
| 0 270 704 | 6/1988 | European Pat. Off. . |
| 0376641 | 7/1990 | European Pat. Off. . |
| 0409364 | 1/1991 | European Pat. Off. . |
| 0464479 | 1/1992 | European Pat. Off. . |
| 0464480 | 1/1992 | European Pat. Off. . |
| 0465910 | 1/1992 | European Pat. Off. . |
| 0 502 509 A1 | 9/1992 | European Pat. Off. . |
| 0 504 915 A1 | 9/1992 | European Pat. Off. . |
| 0 588 671 A1 | 3/1994 | European Pat. Off. . |
| 0 630 613 | 12/1994 | European Pat. Off. . |
| 739089 | 1/1933 | France . |
| 2622430 | 5/1989 | France . |
| 3445738 | 6/1986 | Germany . |
| 3509417 | 9/1986 | Germany . |
| 8633339 | 4/1987 | Germany . |
| 4106823 | 6/1992 | Germany . |
| 584855 | 12/1977 | U.S.S.R. . |
| 2084468 | 9/1981 | United Kingdom . |
| 2 199 914 | 7/1988 | United Kingdom . |
| 2 266 246 | 10/1993 | United Kingdom . |
| WO 85/04568 | 10/1985 | WIPO . |
| WO8603666 | 7/1986 | WIPO . |
| WO 89/01767 | 3/1989 | WIPO . |
| WO8909030 | 10/1989 | WIPO . |
| WO8910096 | 11/1989 | WIPO . |
| WO9204874 | 4/1992 | WIPO . |
| WO93/08747 | 5/1993 | WIPO . |
| WO95/15726 | 6/1995 | WIPO . |
| WO 96/14798 | 5/1996 | WIPO . |

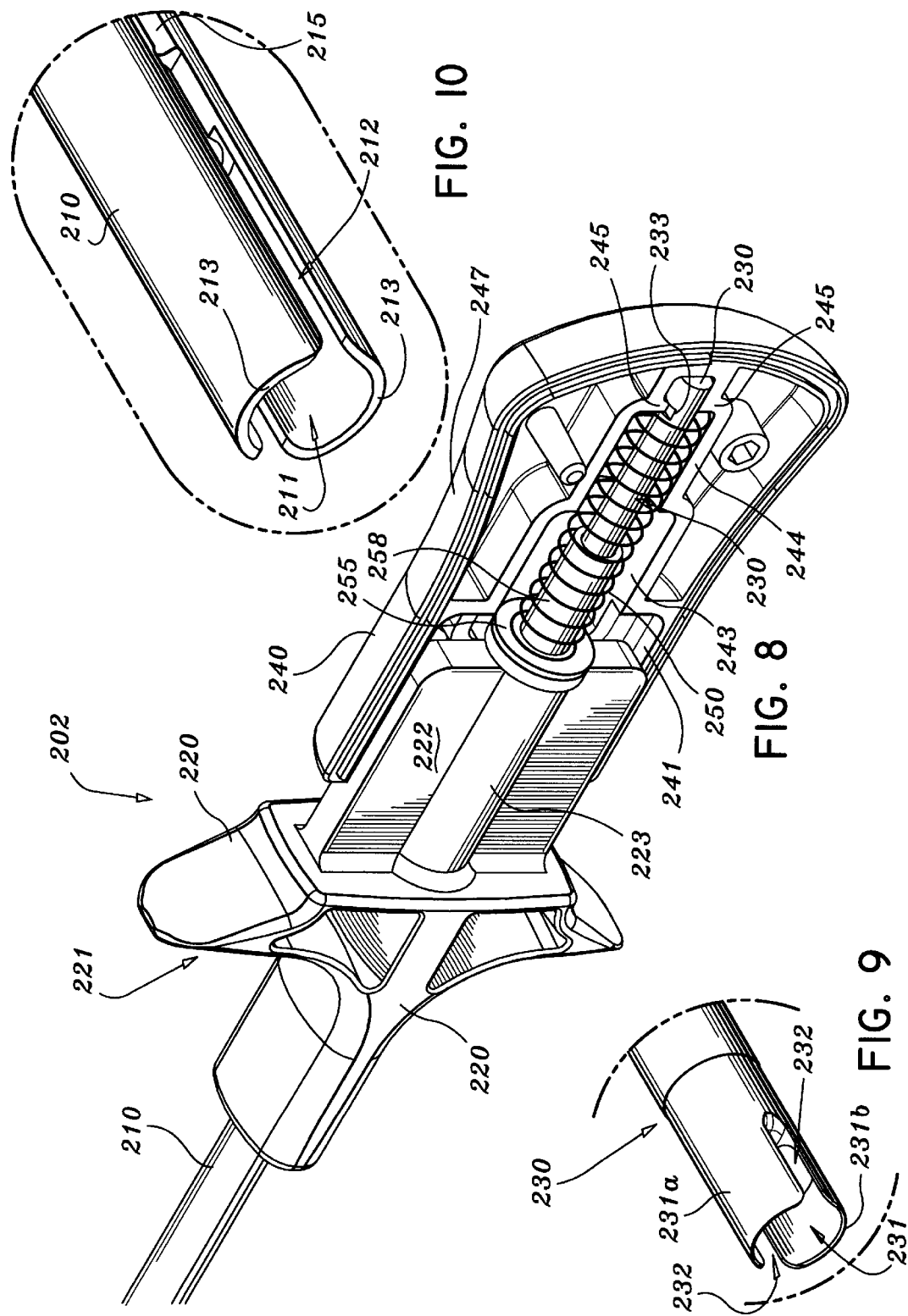

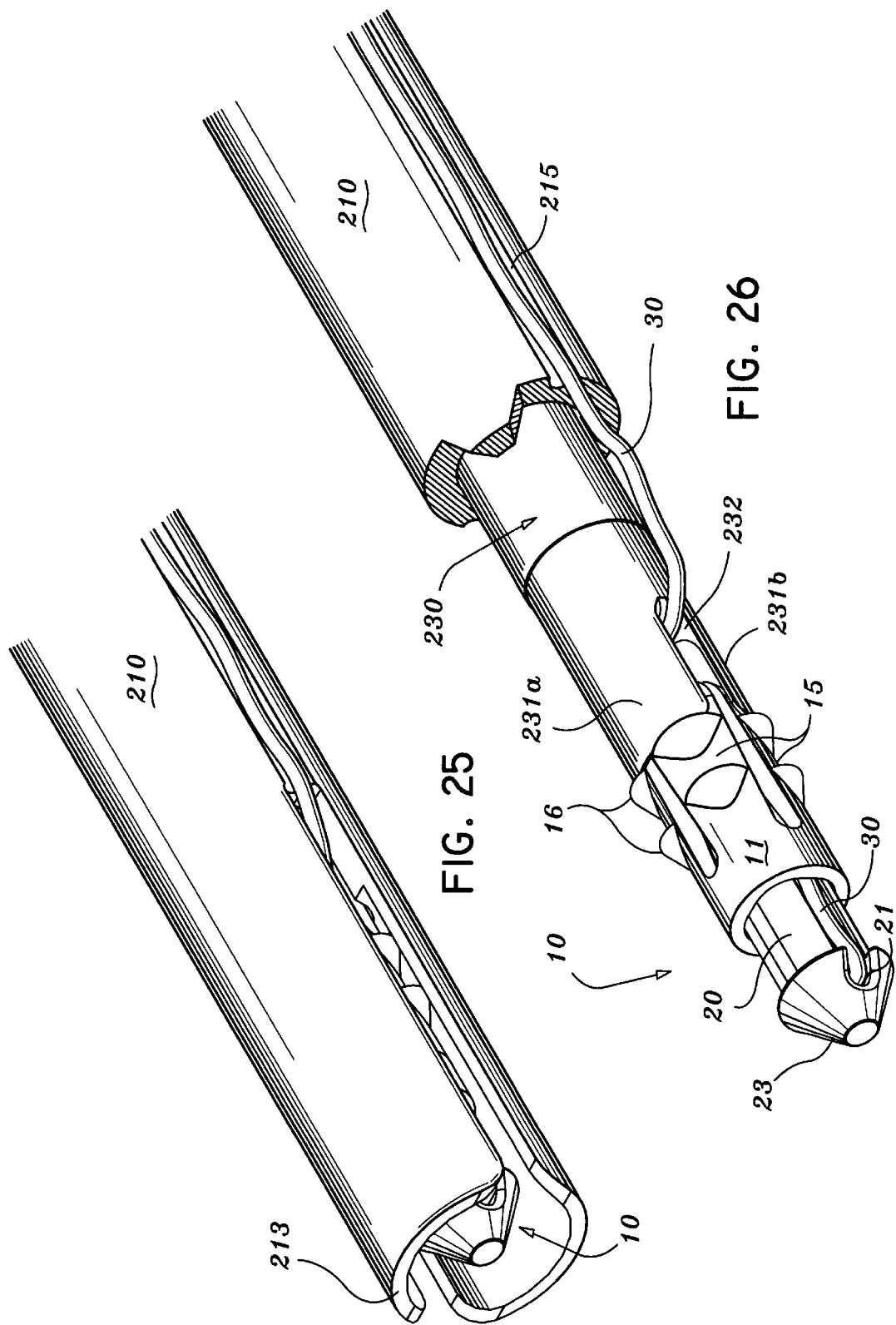

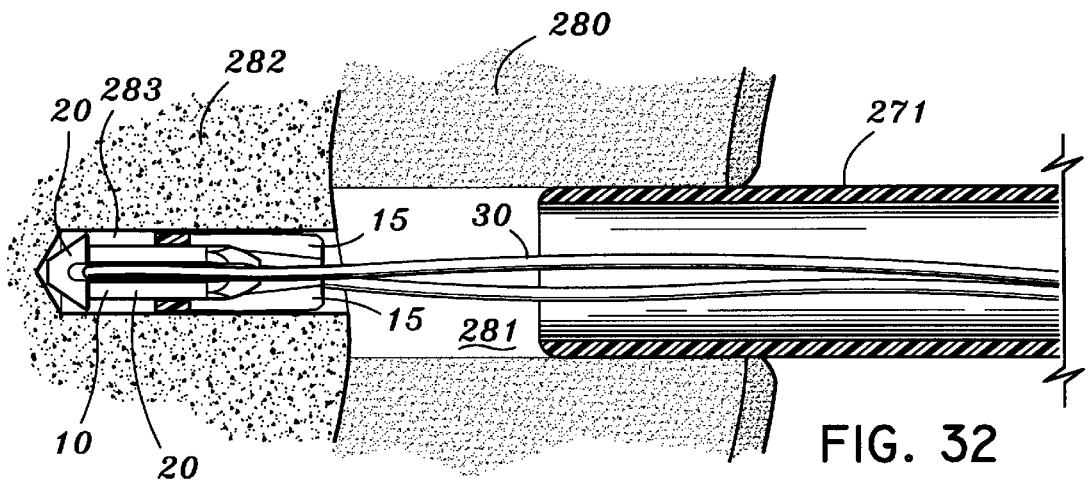
FIG. 32
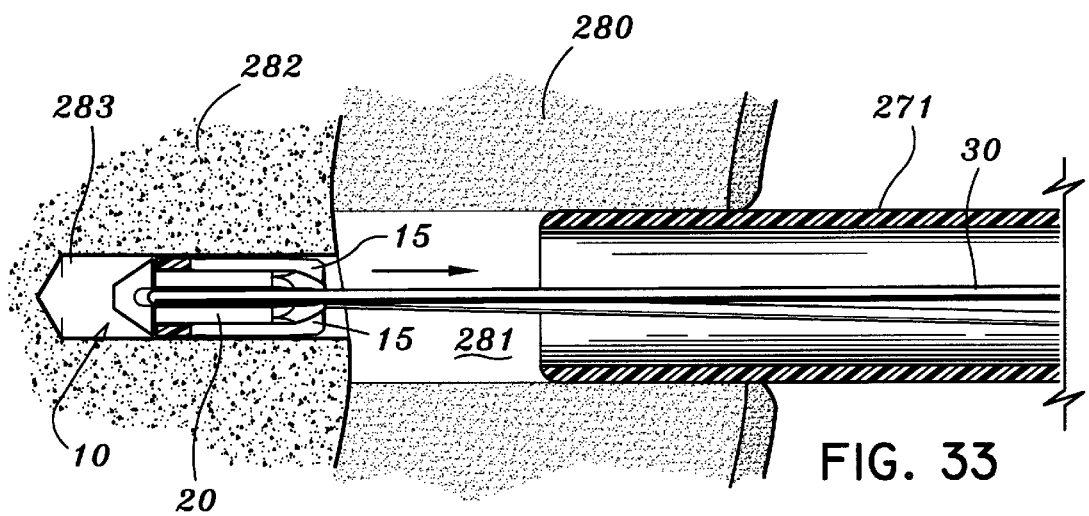
FIG. 33
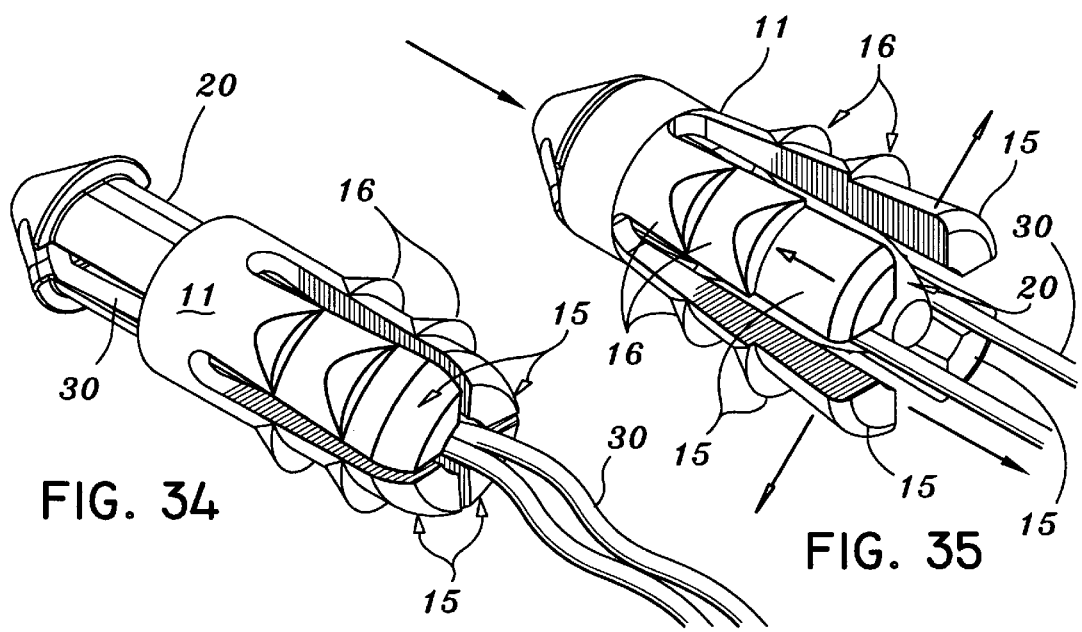
FIG. 34
FIG. 35

SUTURE ANCHOR INSTALLATION SYSTEM WITH INSERTION TOOL

CROSS-REFERENCE TO RELATED APPLICATIONS

This is a continuation of U.S. application Ser. No. 08/919,902 filed Sep. 18, 1998 as a Continued Prosecution Application of U.S. application Ser. No. 08/919,902 filed Aug. 28, 1997, which was filed as a continuation of U.S. patent application Ser. No. 08/726,026 filed Oct. 4, 1996 both abandoned. The entire contents of U.S. application Ser. No. 08/919,902 are herein incorporated by reference.

BACKGROUND

1. Technical Field

The present disclosure relates to a suture anchor installation system and, more particularly, to a suture anchor installation system including a suture anchor insertion tool engaging a two-piece suture anchor having a suture and needle assembly.

2. Discussion of Related Art

During surgery, it is often necessary to attach muscle tissue or prosthetic implants to bone. Suture anchors are used in the art to facilitate such attachment by securing a suture to bone. Generally, an anchor is implanted into a hole pre-drilled into a bone mass. A suture engaged by the suture anchor extends from the bone and is used to stitch the muscle tissue or prosthetic device to the bone. Suture anchors find particular use in joint reconstruction surgery, especially during attachment of ligaments or tendons to bones in the knee, shoulder, and elbow.

Several systems have been proposed in the art to aid the surgeon in implanting a suture anchor into a bone. One such system, shown in U.S. Pat. No. 5,100,417 to Cerier et al., comprises a driver having a handle and elongated shaft. An anchor snap fits on the end of the shaft over an anti-rotation pin which mates with slots in the anchor. A suture engaged in the anchor has its ends affixed to posts extending from the driver handle. The Cerier et al. system suffers from the disadvantage that the driver does not accommodate sutures having preattached needles. Thus, use of this system requires threading the suture into a needle, a time-consuming procedure for the surgeon.

Another suture anchor installation system is shown in U.S. Pat. No. 5,002,550 to Li. The Li system comprises a suture anchor having a normally curved barb capable of being elastically deformed to a substantially straight configuration. The suture anchor engages a suture having a pair of surgical needles attached to its ends. The installation tool is adapted to receive the surgical needles and a pair of grooves formed in the tool's outer surface. The tool additionally provides a member for selectively covering and uncovering the needles received in the grooves.

The Li suture anchor installation system uses shape-memory alloys to fabricate the suture anchors. Such materials are not bioabsorbable. Additionally, the normally curved barb of the Li system protrudes from the installation tool during positioning of the anchor.

Yet another suture anchor installation system is disclosed in U.S. Pat. No. 5,354,298 to Lee et al. The suture anchor installation system comprises a suture anchor assembly engaged with a suture anchor insertion tool. The suture anchor assembly features a two-piece suture anchor for insertion into a pre-drilled hole in a bone and at least one suture having at least one surgical needle affixed thereto. The two-piece suture anchor has a setting pin slidably engaged within an engagement member having barbed legs expandable in response to proximal movement of the setting pin. The suture anchor insertion tool includes a body portion and a distally extending shaft portion. An annular region of the distal end of the shaft portion engages the legs of the suture anchor engagement member. A channel in the shaft portion aligns with a channel in the body portion to accommodate the suture. Needle-retaining assemblies located on the body portion of the suture anchor insertion tool engage the surgical needle or needles attached to the suture.

The suture anchor installation tool of the Lee et al. U.S. Pat. No. 5,354,298 is packaged in a preloaded condition. The package is opened in the operating room and the installation tool is removed from the package and used to apply the suture anchor. Operating room conditions are not conducive to manually reloading the Lee et al. installation tool with a fresh suture anchor for reuse of the installation tool. In the event that a second suture anchor must be applied another suture anchor installation tool package is opened and a new preloaded suture anchor installation system is used.

It would be advantageous to use a single installation tool during an operation and reload it as appropriate. What is needed is a mechanism which facilitates reloading of the suture anchor installation tool in the operating room.

SUMMARY

The suture anchor installation system described herein includes a tool for inserting the suture anchor. The tool includes a handle portion having a grip portion, and a trigger portion slidably mounted to the grip portion, the trigger portion having an axial bore. The apparatus further includes an elongated operating portion with an outer tube disposal within the bore of the trigger portion and a rod slidably disposed within the bore of the outer tube. The outer tube is movable between distal and proximal positions, and is resiliently biased to the distal position. The rod has a proximal end fixedly attached to the grip portion and a distal end with an opening configured to engage a suture anchor.

BRIEF DESCRIPTION OF THE DRAWINGS

Various embodiments are discussed below with reference to the drawings, wherein:

FIG. 8 is a perspective view of the interior of the handle portion of the installation tool;

FIGS. 9 and 10 are perspective views of the distal ends of the inner shaft and outer tube, respectively, of the installation tool;

FIGS. 25 and 26 are perspective views showing retention of the suture anchor in the installation tool, FIG. 26 being a partial cut-away view;

FIGS. 30 to 33 are sequential sectional side views illustrating implantation of a suture anchor; and, FIGS. 34 and 35 are perspective views illustrating activation of the suture anchor to expand the legs.

DETAILED DESCRIPTION OF PREFERRED EMBODIMENTS

The suture anchor installation system is provided for securing a suture to hard tissue, such as bone. The suture can be used to attach soft tissue or a prosthetic device to the bone. As used herein, the term "soft tissue" refers to all of the non-bony tissues within an organism including, but not limited to, muscle, cartilage, skin, tendons, ligaments, etc. The term "prosthetic device" refers to any article implanted in the body including, but not limited to, artificial ligaments, muscles, joints, etc.

Moreover, the suture anchor installation system is advantageously used in minimally invasive surgical procedures such as laparoscopic, endoscopic, or arthroscopic operations in which the operating instrumentation is deployed through narrow cannulas inserted through small incisions or openings in the patient's body. Alternatively, the suture anchor installation system may also be used in standard open surgical procedures.

The suture anchor installation system described herein comprises a suture anchor assembly retained in a disposable loading unit, and a suture anchor installation tool. The suture anchor assembly features a two-piece suture anchor for insertion into a pre-drilled hole in bone and at least one suture having at least one surgical needle affixed thereto. The two-piece suture anchor comprises a setting pin slidably engaged within an expandable engagement member which grips the sides of the hole drilled in the bone. In a preferred embodiment, this engagement member is an expandable socket. The expandable socket includes an apertured body portion having at least two barbed legs extending proximally therefrom. The legs are radially expandable in response to proximal movement of the setting pin. Suture anchors suitable for use in the suture anchor installation system are described in U.S. Pat. No. 5,354,298. The suture can be "double-armed", i.e. a needle can be attached to each of the two ends of the suture to facilitate knotting the suture and securing the soft tissue to the bone.

Figure 1:
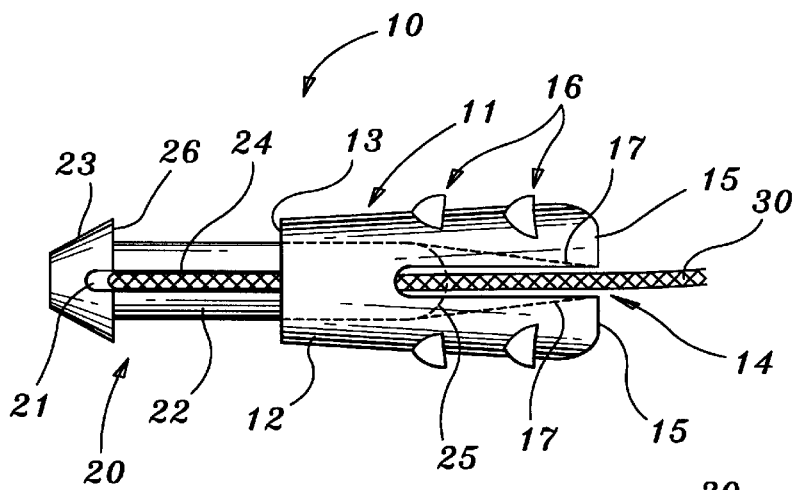
FIG. 1 is a side view of a suture anchor.
Figure 2:
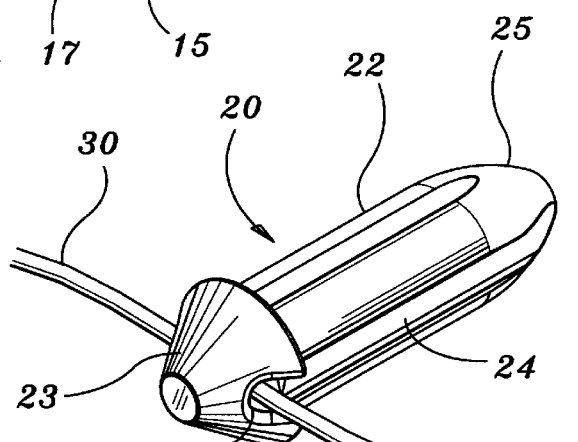
FIG. 2 is a perspective view of the setting pin of the suture anchor with a suture disposed therethrough.
Figure 3:
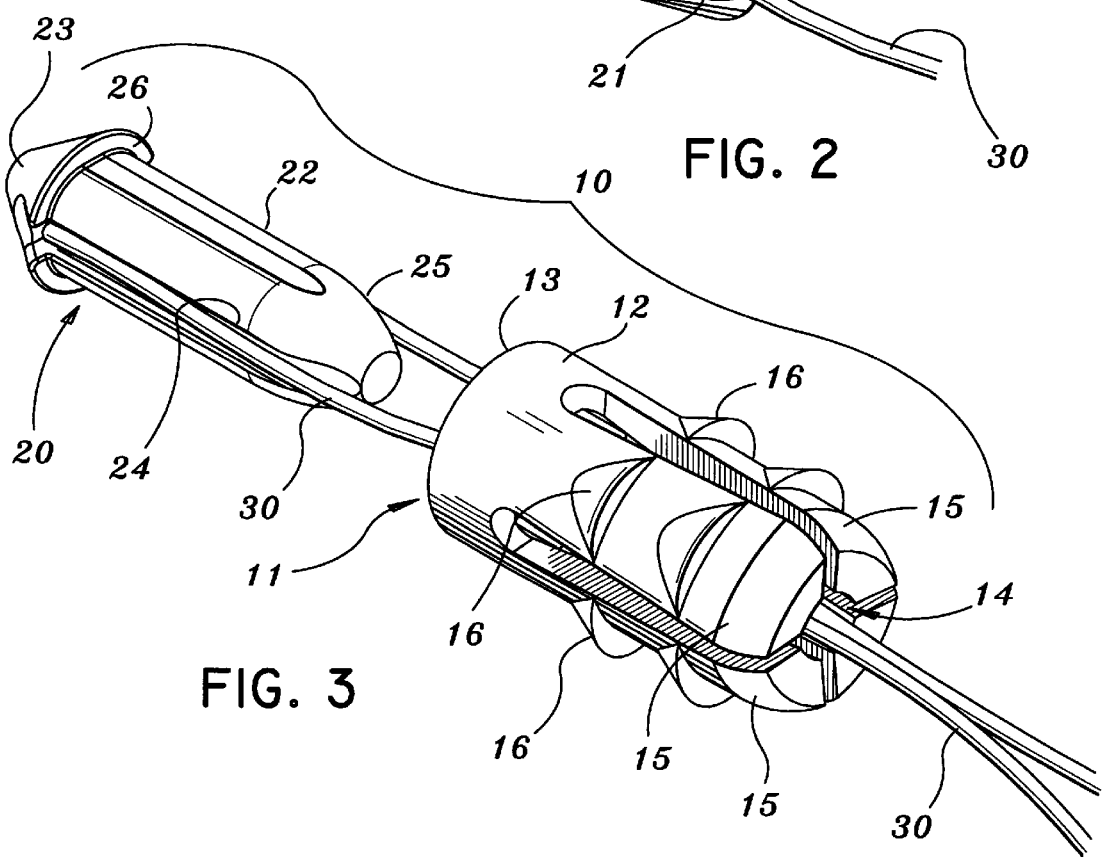
FIG. 3 is an exploded view showing the suture retained by the setting pin.

More particularly, referring now to FIGS. 1 to 3, a preferred two-piece suture anchor 10 is illustrated. Preferably, the suture anchor 10 is fabricated from a synthetic bioabsorbable polymeric resin such as polymers of glycolide, lactide, caprolactone, p-dioxanone, trimethylene carbonate and physical and/or chemical combinations thereof. The suture is preferably a size 2 suture formed of Dacron. However, it is anticipated that the suture may also be formed from a synthetic bioabsorbable polymeric resin.

The suture anchor 10 includes a socket 11 for insertion distally into a pre-drilled hole in bone or hard tissue. The socket has a body portion 12 terminating in an annular distal end surface 13 which acts as a stop surface as discussed below, an axially extending aperture 14, and at least two (preferably four) legs 15 extending proximally from the body portion 12. Legs 15 are normally radially expandable in response to movement of a setting pin 20 slidably disposed within the axially extending aperture 14 as explained more fully below with reference to FIGS. 34 and 35. The setting pin 20 has a suture attachment feature and is movable between a distal position with respect to socket 11 wherein socket legs 15 are not expanded, and a proximal position with respect to the socket 11 wherein socket legs 15 are urged to a radially spread-out configuration.

More particularly, setting pin 20 includes a shaft portion 22, a tapered tip 23 with preferably a substantially frusto-conical shape and a proximal facing abutment surface 26, and a transverse aperture 21 near the distal end for receiving a suture 30. Proximal end 25 is rounded and acts as a carrying surface. The setting pin 20 also includes two longitudinal notches 24 extending along shaft portion 22 along which suture 30 is disposed.

Proximally extending legs 15 of the socket 11 include barbs 16 on their outer surface and an inwardly inclined inner surface 17. When setting pin 20 is moved proximally from its initial distal-most position (i.e. by pulling suture 30), the rounded proximal end 25 of the shaft portion cams against the inner surface 17 and thereby urges legs 15 to expand radially outward. At the most proximal position of the setting pin 20, the abutment surface 26 of tapered tip 23 contacts distal end surface 13 of the socket. Setting pin 20 is thereby stopped from further proximal movement. A matching non-circular cross section of the pin and socket aperture may be employed to prevent suture interference with the setting action by preventing free rotation of the setting pin within the axial aperture of the socket and by locating the suture between the legs 15 of the socket.

Figure 4:
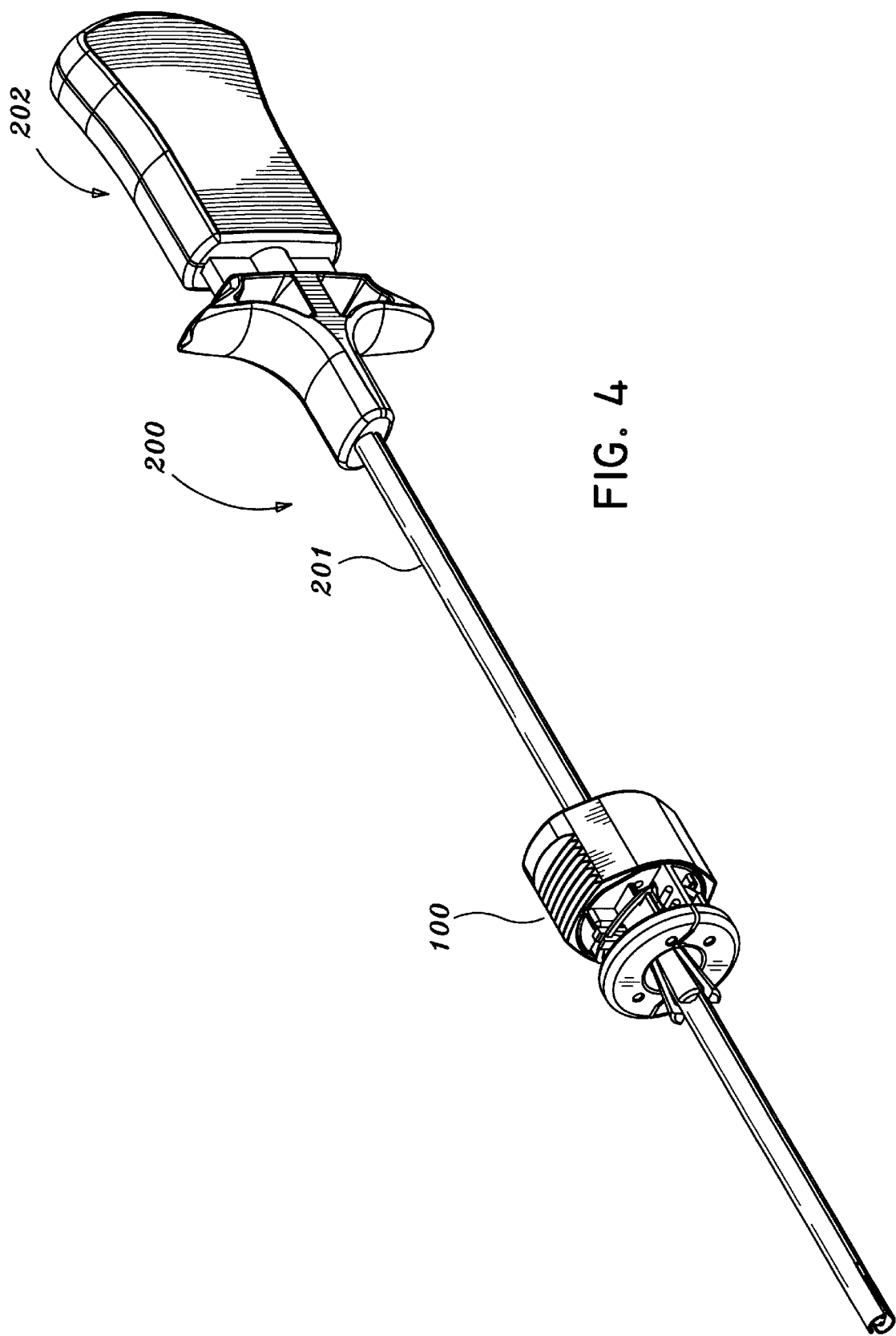
FIG. 4 is a perspective view of the suture anchor installation system with disposable loading unit.
Figure 5:
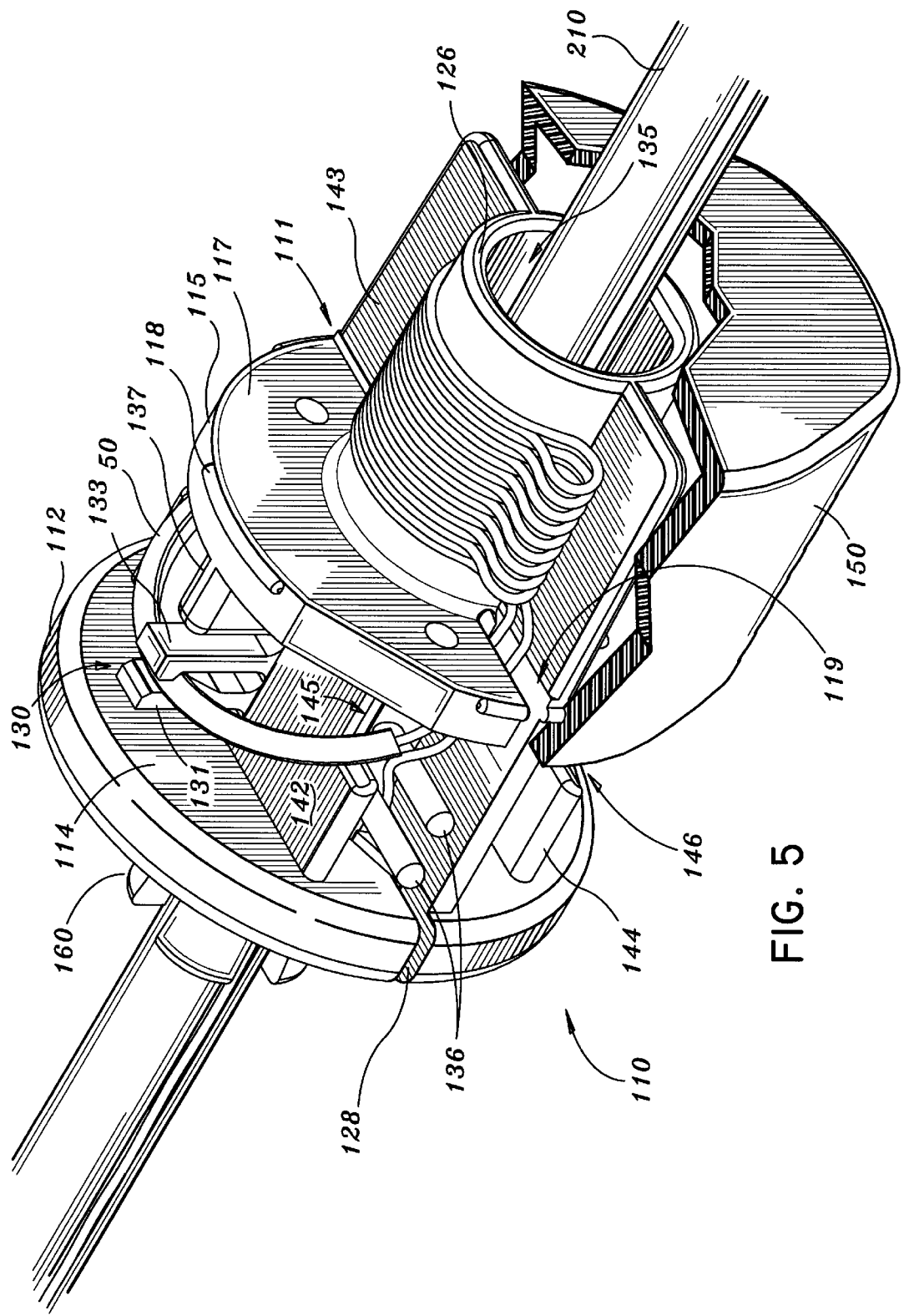
FIG. 5 is a cutaway partly sectional perspective view of the disposable loading unit.
Figure 6:
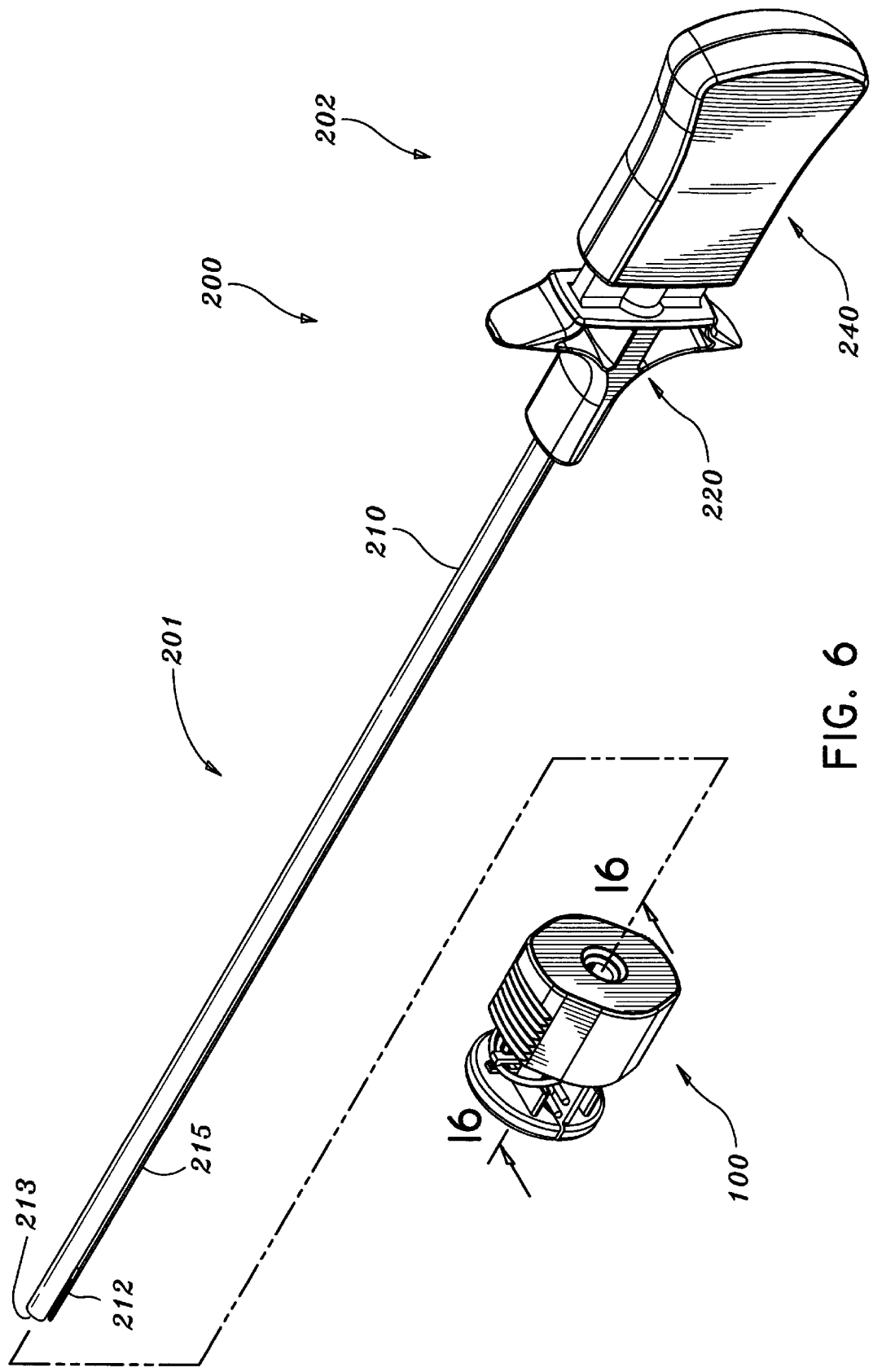
FIG. 6 is a perspective view of the loading unit and installation tool.

Referring now to FIG. 4, the suture anchor installation system includes a disposable loading unit 100 and an installation tool 200. The disposable loading unit 100 is removably engageable within installation tool 200 by mounting onto the distal operating portion 201.

Referring now to FIGS. 4, and 6–10, the installation tool 200 includes a distal elongated operating portion 201 and a proximal handle portion 202.

The operating portion 201 includes an outer tube 210 which extends longitudinally from trigger portion 220 and is movably mounted thereto. Outer tube 210 includes an axial bore for receiving inner shaft 230, discussed below. At the distal end opening 211 of the bore there are two lengthwise extending slots 212 (see, FIG. 10) which divide the distal end portion of the outer tube 210 in two partitions. The outer tube terminates in distal edges 213 which provide a camming function discussed below. Lengthwise notches 215 for receiving a length of suture extend from proximal end surface 214 of the outer tube to the proximal edges of slots 212.

The inner shaft 230 is disposed within the bore of outer tube 210 and includes a mouth 231 having partitions 231a and 231b defined by longitudinal slots 232 (See, FIG. 9). The inner shaft 230 is fixedly attached to the handle portion 240 by means of notch 233. Mouth 231 of the inner shaft is adapted to engage the proximal end portion of the legs 15 of socket 11, and to hold the suture anchor 10 temporarily until the suture anchor 10 is inserted into the bone site.

The handle portion 202 includes a trigger portion 220 and a handle 240 having an outer gripping surface 247.

Figure 7:
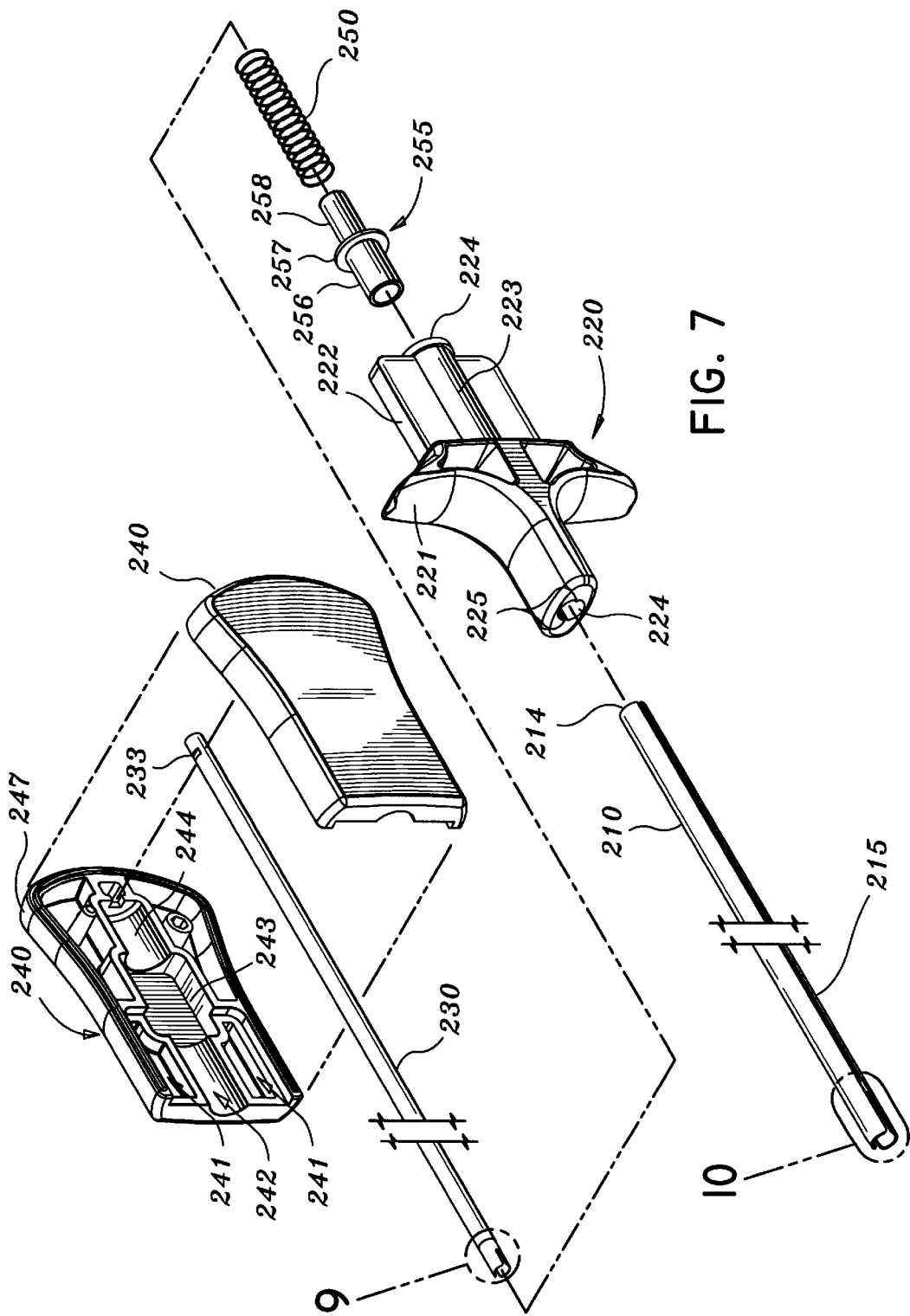
FIG. 7 is an exploded perspective view of the installation tool.
Figure 11:
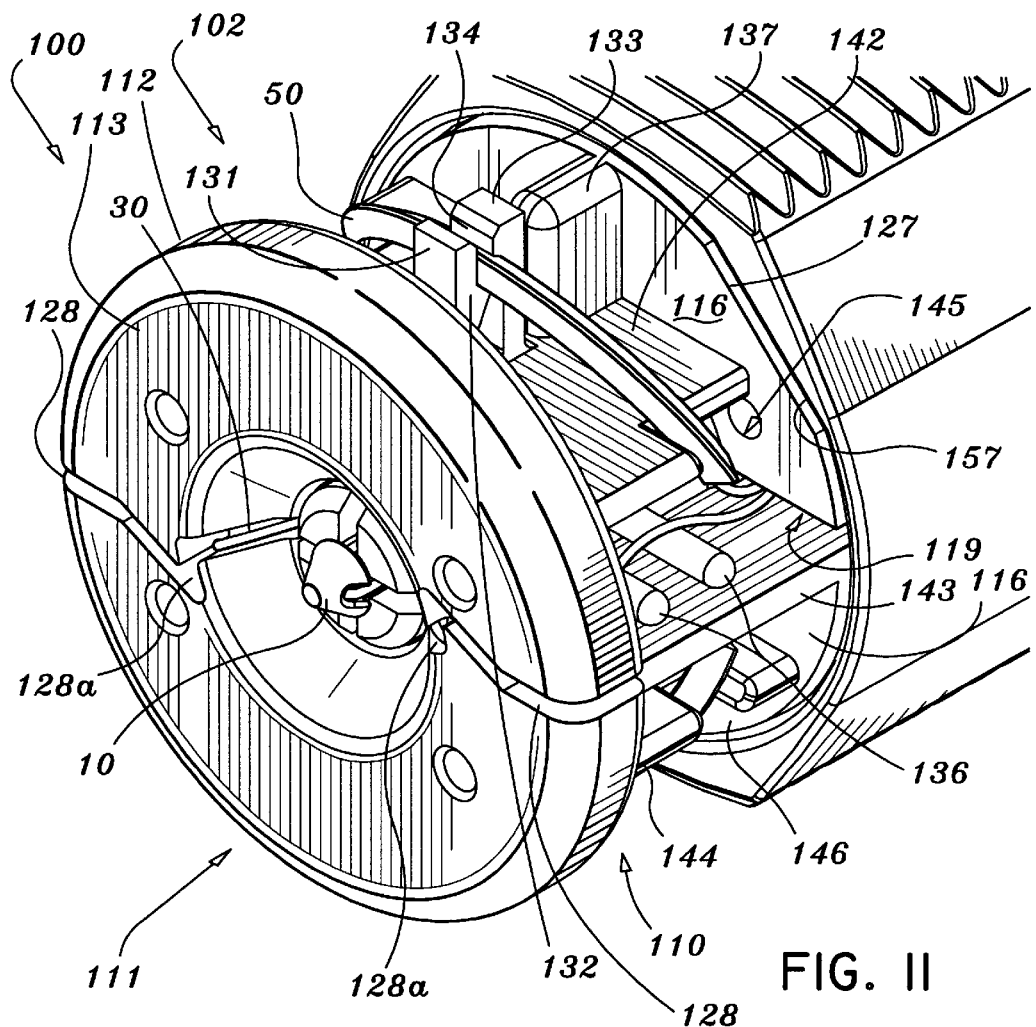
FIG. 11 is a perspective view of the disposable loading unit with needles and suture loaded therein.
Figure 12:
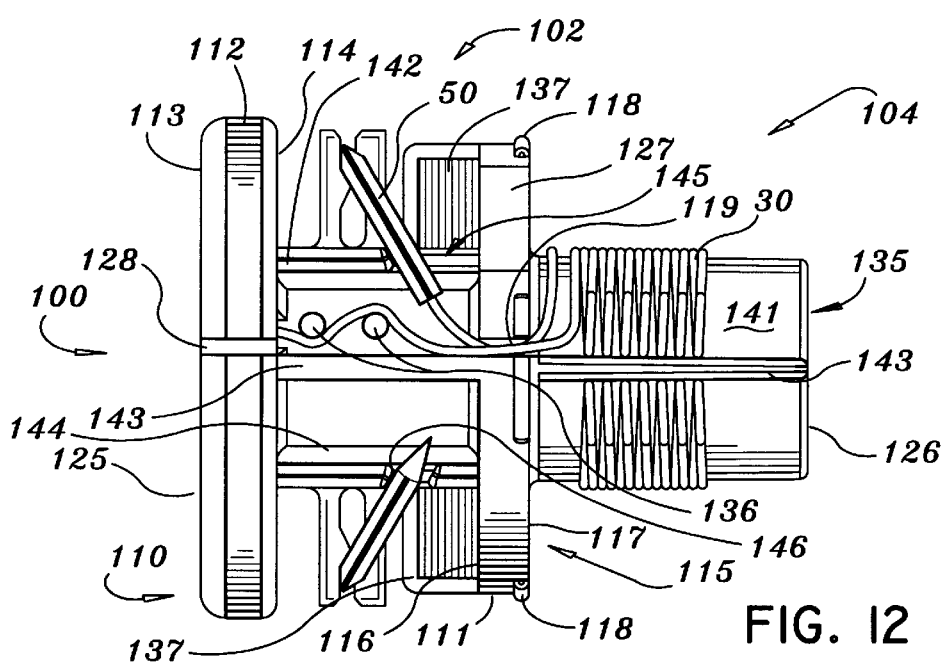
FIG. 12 is a side view of the disposable loading unit with needles and suture loaded therein.

Referring to FIGS. 7 and 8, trigger 220 includes a frame having a finger rest 221 and a substantially rectangular body portion 222. The rectangular body 222 is adapted to be slidably received into distal inner chamber 241 of handle 240. Tubular section 223 extends along body 222 and is adapted to fit within cylindrical bore 242 of handle 240. An axial bore 224 extends longitudinally through trigger 220 and receives outer tube 210. Ribs 225 extending longitudinally on the inside surface of bore 224 engage notches 215 to prevent rotation of outer tube 210 relative to trigger 220.

The proximal end 214 of the outer tube is fixedly mounted to the distal portion 256 of collar 255 (see, FIG. 7). Collar 255 also includes a flange 257 and a proximal portion 258. Distal portion 256 is slidably disposed within axial bore 224, but flange 257 provides a stop surface and limits further distal entry of collar 255 into bore 224. Proximal portion 258 is received into the center of helical compression spring 250.

Collar 255 is at least partially disposed within middle chamber 243 of handle 240. Spring 250 extends into proximal chamber 244 of the handle. The proximal end of spring 250 abuts a surface at the proximal end of chamber 244. The distal end of spring 250 abuts flange 257 of the collar and thereby exerts a distally directed biasing force on the collar 255 and outer tube 210 when in a compressed state.

Inner shaft 230 extends through outer tube 210, through the axial bore of collar 255, and into and through chambers 243 and 244 of handle 240. Projections 245 in the handle are adapted to engage notches 233 to secure the inner shaft 230 to the handle 240.

The outer tube 210 is formed from clear polycarbonate to permit the surgeon to see the suture anchor 10 through the outer tube 210, and inner shaft 230 is preferably fabricated from a biocompatible metal such as stainless steel or titanium. Handle 240 and trigger 220 may be fabricated by, for example, injection molding from polymeric resin having the mechanical properties suitable for the use described herein. Suitable polymers include acrylics, and/or polycarbonates, for example. Handle 240 and trigger 220 are preferably fabricated in two parts which are then assembled and fastened together by adhesive bonding, or rivets, screws or other such fastening means.

Referring now to FIGS. 5, 11, 12, and 13, the disposable loading unit 100, shown in combination with the suture anchor 10, suture 30 and needles 50, includes a housing 110, a removable cap 150, and a spring biased collet 160 for releasably holding the suture anchor 10.

Housing 110 includes a body 111 having a distal flange 112. The distal flange 112 includes a distal surface 113 corresponding to the distal end 125 of housing 110, a proximal surface 114, and lateral slots 128 which include angled portions 128a to retain the suture 30. Medial flange 115 includes distal surface 116, proximal surface 117, and snap fit ridges 118 extending at least partially around the circumferential outer edge of the flange 115. Medial flange 115 also includes flattened surfaces 127 around its circumferential rim, surfaces 127 being adapted to engage corresponding flattened surfaces 157 in the cap to inhibit relative rotation between the cap 150 and housing 110. A distal chamber 102 is at least partially defined by proximal surface 114 of the distal flange, and distal surface 116 of the medial flange, and provides a space for the storage of curved needles 50, one needle being attached to each end of suture 30. A proximal chamber 104 is at least partially defined by proximal surface 117 of the medial flange, and provides space for the storage of suture 30. Radial slots 119 in medial flange 115 provide access for the suture 30 to extend from the distal chamber 102 to the proximal chamber 104. Housing 110 also includes an axial bore 135 extending from the distal end 125 to the proximal end 126 of housing 110. Buttress plates 137 extend distally from the medial flange 115 and provide support therefor.

The body 111 of housing 110 includes a central tubular portion 141 having an inner wall defining the axial bore 135. Also included as part of the body 111 are upper shelf 142, middle shelf 143, and lower shelf 144. The terms "upper" and "lower" are used relative to each other herein with reference to the drawings (See, e.g. FIG. 12), and not to any external frame of reference. The upper and lower shelves 142, 144 each include, on opposite sides, a proximal cutaway portion 145 to accommodate the butt end of the surgical needle 50, and a medial cut away portion 146 to accommodate the pointed tip of the curved surgical needle 50. The proximal cut away portions 145 are in the vicinity of respective radial slots 119 to allow the suture 30 attached to the butt end of the needle to extend through radial slot 119 into the proximal chamber 104. Upper and lower shelves 142, 144 occupy the distal chamber 102. The middle shelf 143 extends to the proximal end 126 of housing 110.

Suture 30 follows a path, for example, extending from the butt end of one needle 50 mounted in needle park 130 on upper shelf 142, through one of the radial slots 119 in the medial flange, and into proximal chamber 104 where part of its length is stored as a coil above middle shelf 143. Suture 30 then extends back out through radial slot 119 across distal chamber 102 around lateral posts 136 and through one lateral slot 128 in the distal flange 112 whereupon it extends across collet 160 and into and through suture anchor 10. From the suture anchor 10, suture 30 follows a reverse path on the other side of the housing 110, extending through lateral slot 128 on the other side of distal flange 112, around the lateral posts 136 on the other side (not shown) of the housing, across distal chamber 102, through the opposite side radial slot 119, and into proximal chamber 104 where a length of suture 30 is stored below middle shelf 143. Thereafter, suture 30 returns through the opposite side radial slot 119 and is attached to the butt end of the second needle 50 mounted to a needle park 130 on the lower shelf 144.

Figure 16:
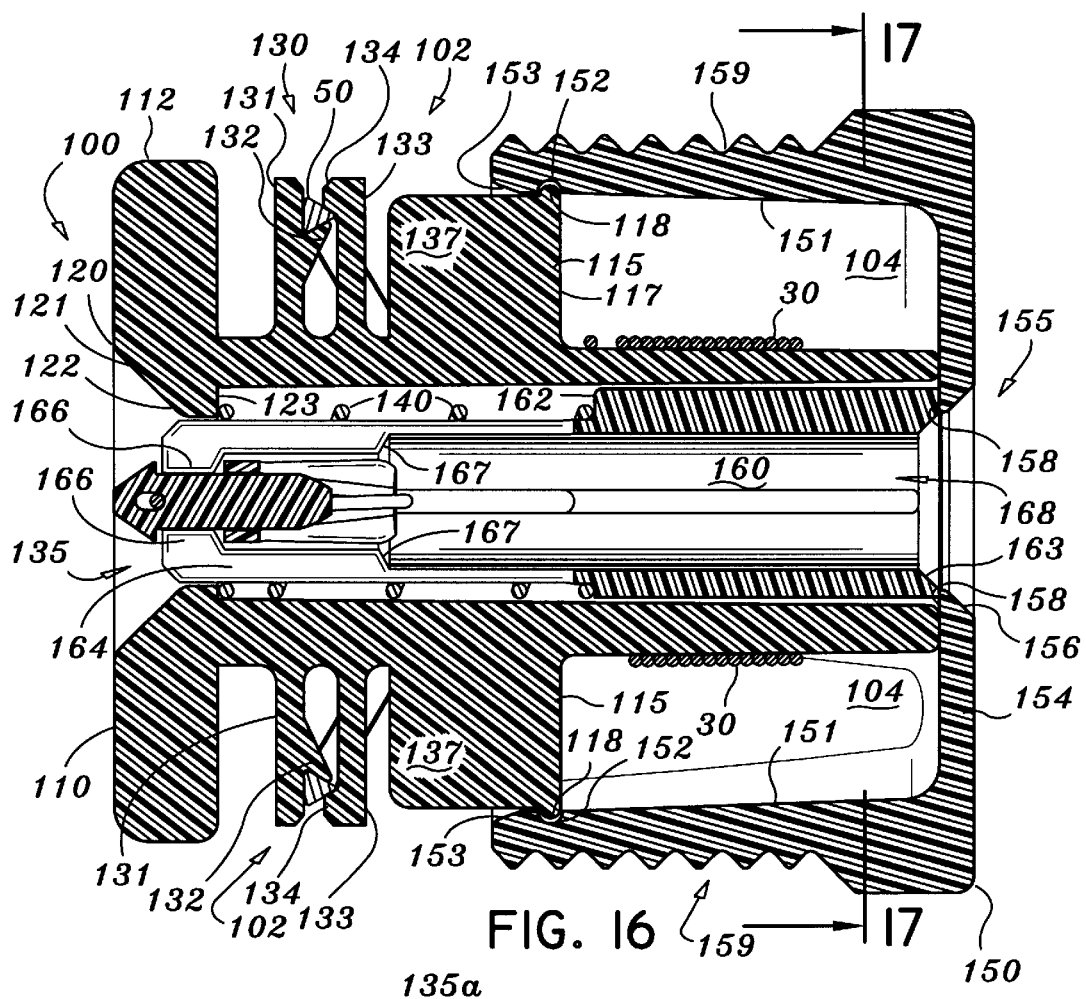
FIG. 16 is a side sectional view of the disposable loading unit showing retention of the suture anchor taken along line 16—16 in FIG. 6.

Referring also now to FIG. 16, the distal flange 112 includes a rim portion 120 extending circumferentially around the distal opening of axial bore 135 and having a bevelled distal surface 121, and a radially inward extending lip 122 having a proximally facing annular surface 123. Housing 110 preferably includes needle parks 130 extending radially outward from the body portion 111 between the distal and medial flanges 112 and 115, respectively, so as to retain a curved needle 50 on the upper and lower shelves 142 and 144, respectively within the distal annular space 102.

Each needle park 130 comprises a distal upright post 131 having a needle supporting projection 132, and a proximal upright post 133 having a needle retaining projection 134. The posts 131, 133 are resilient and allow the needle 50 to snap fit into the space between the projections 132, 134 for convenient removal by the surgeon.

Figure 13:
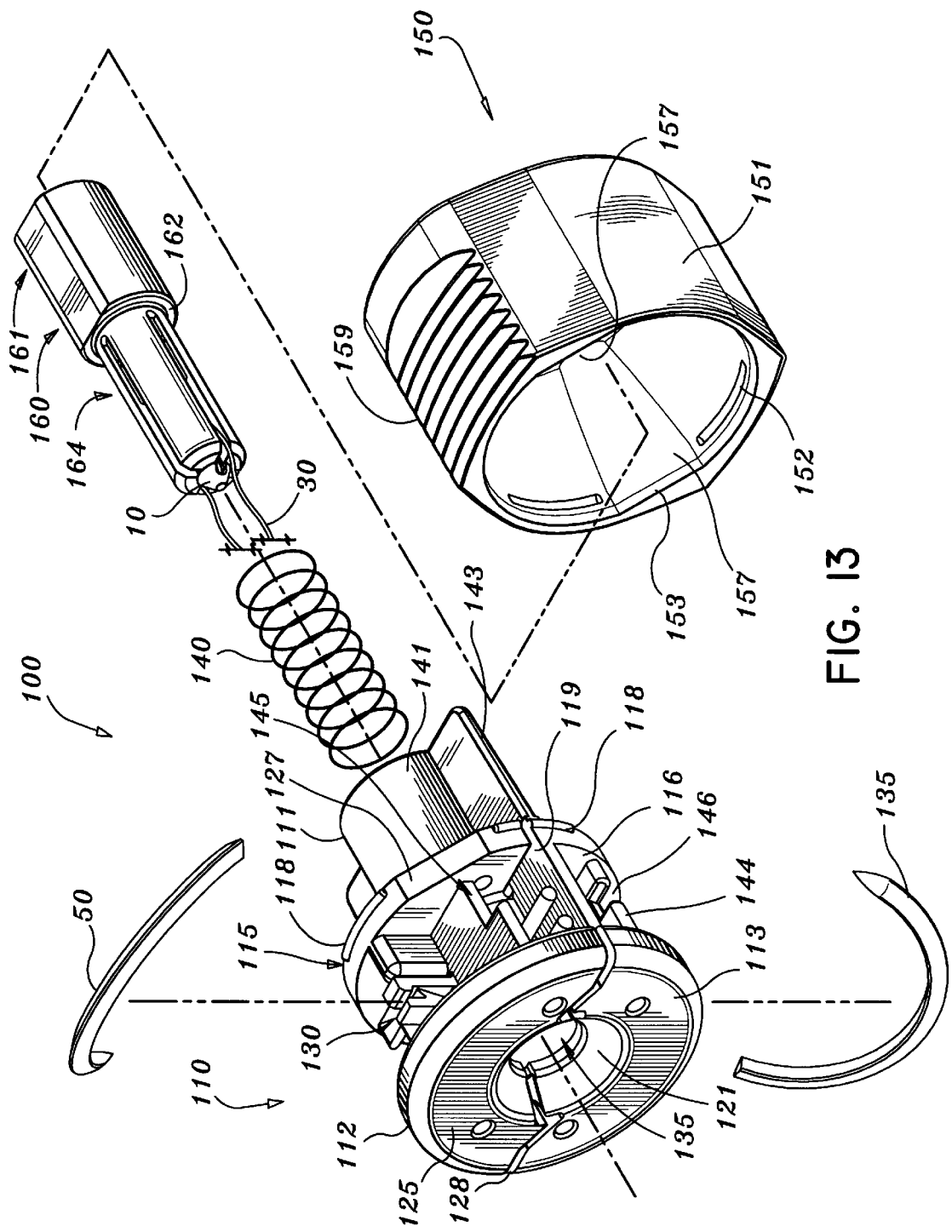
FIG. 13 is an exploded perspective view of the disposable loading unit.
Figure 15:
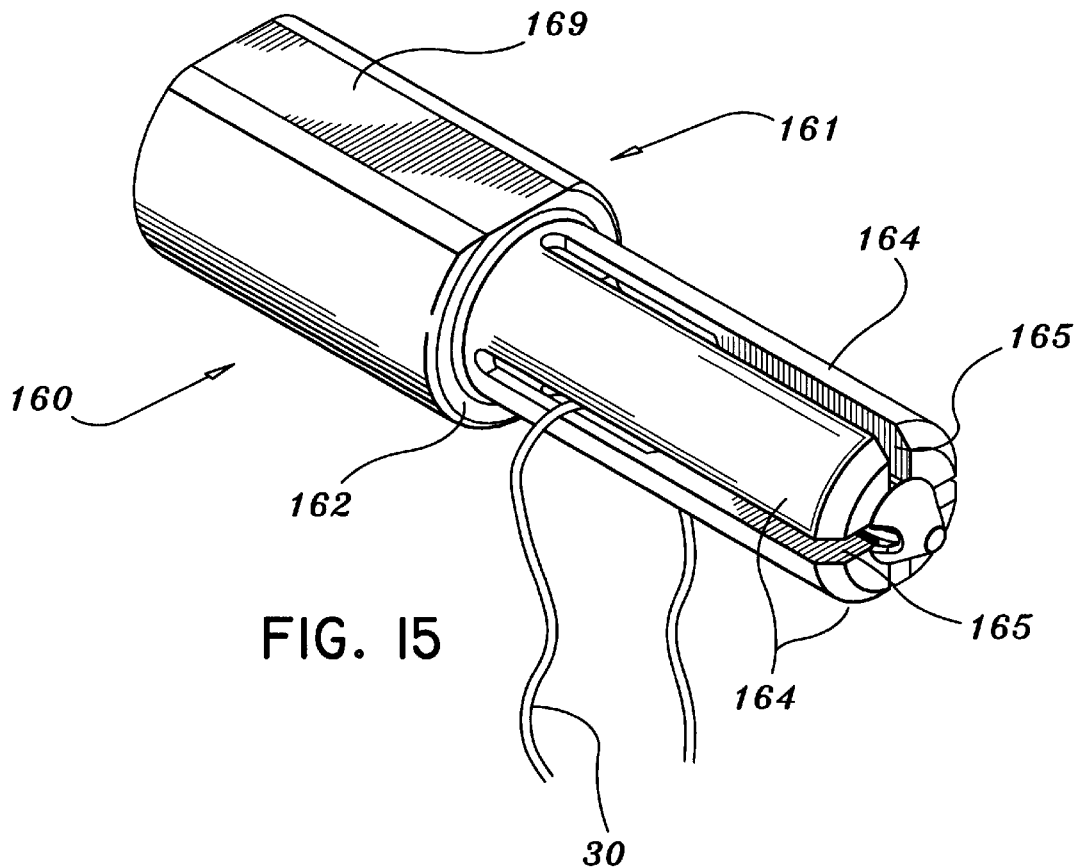
FIGS. 14 and 15 are perspective views illustrating positioning of the suture anchor within the collet.
Figure 14:
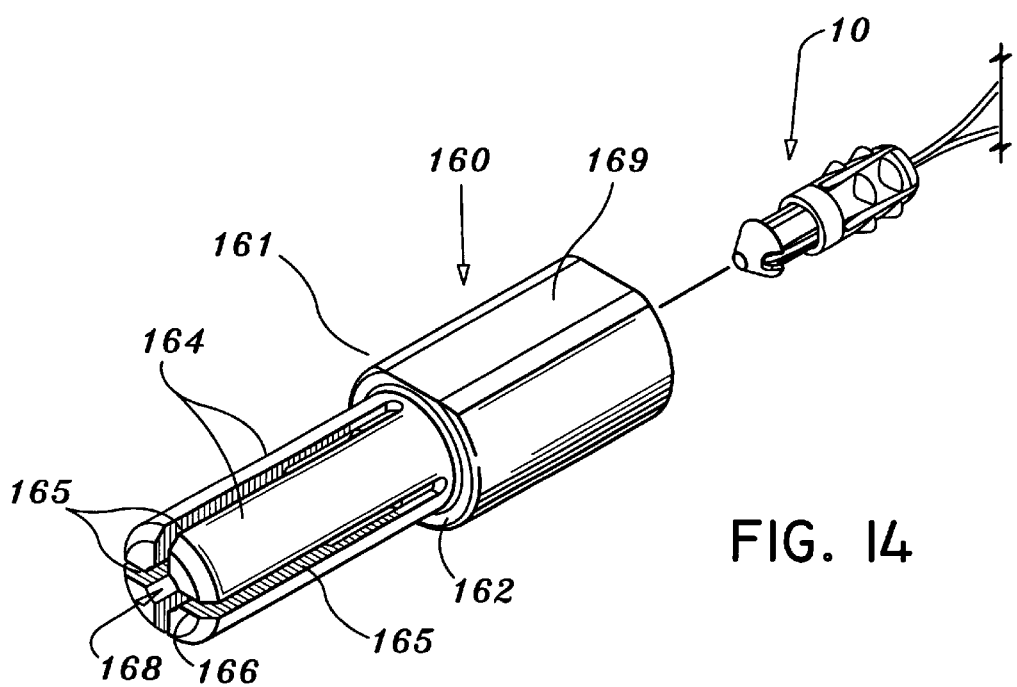

Referring to FIGS. 13 and 16, cap 150 is removably attachable to housing 110 and includes a cylindrical barrel portion 151 and a circular back wall 154. The distal edge of the barrel portion 151 includes a bevelled inner surface 153 to facilitate engagement of the barrel portion 151 with medial flange 115, and notches 152 which engage and receive snap fit ridges 118 to removably secure the cap 150 to the housing 110. Back wall 154 includes a central aperture 155 defined by bevelled proximal rim 156. A portion of the bevelled rim 156 extends partially across the proximal opening of axial bore 135 so as to present a distal facing surface 158 across bore 135 to retain the collet 160. Cap 150 includes flattened inner surfaces 157 corresponding to flattened surfaces 127 of the medial flange 115 (See, FIG. 13). Upper and lower ridges 159 facilitate manual grasping and holding of the cap by the surgeon.

Referring now to FIGS. 13–16, the collet 160 is slidably mounted in axial bore 135 and has a generally cylindrical body portion 161 and at least two, and preferably four, arms 164 extending distally therefrom. The body portion 161 has a planar surface 169, which, in conjunction with a corresponding planar surface in bore 135 of the housing, inhibits rotation of the collet 160 relative to the housing 110. Arms 164 are separated from each other by longitudinally extending slots 165. Bore 168 extends axially through the collet 160. At the proximal opening of bore 168 the body portion 161 includes a bevelled rim 163 which aligns with bevelled rim 156 of the cap when collet 160 is in its most proximal position within the bore 135. Collet 160 is resiliently biased to this most proximal position by helical compression spring 140 which surrounds arms 164. Spring 140 is positioned within the space between the outer surface of arms 164 and the inner surface of the axial bore 135. Distal surface 162 of the collet body portion 161 and proximal surface 123 of the housing distal flange 112 provide stop surfaces between which spring 140 is disposed.

Collet arms 164-include a suture anchor holding portion 166, which is adapted to engage the setting pin shaft 22 between proximal surface 26 of the tapered tip 23 and the distal end surface 13 of the socket when the setting pin 20 is in its distal-most position with respect to the socket 11.

The collet 160 is slidably movable from its initial proximal-most position against the biasing force of spring 140 to a distal position wherein the arms 164 are at least partially disposed outside of axial bore 135. Arms 164 can be radially spread apart when collet 160 has been moved to its distal-most position. Each arm 164 of the collet includes an interior bevelled rim 167 which serves as a camming surface. Rim 167 is contacted by the distal edge 213 of the outer tubular member 210 of the suture anchor installation tool 200. As will be illustrated below, as the inserter 200 is moved distally, collet 160 and suture anchor 10 are pushed distally forward until distal surface 162 completely compresses spring 140 and is thereby stopped from moving distally further. At this configuration arms 164 of the collet are outside the housing 110 and beyond rim 121 of the distal flange 112. Further force distally exerted upon bevelled camming rim 167 will tend to cause arms 164 to splay, or expand radially outward. Expansion of arms 164 in such a manner thereby releases the suture anchor 10 gripped by the distal holding portion 166 of the arms.

Figure 17:
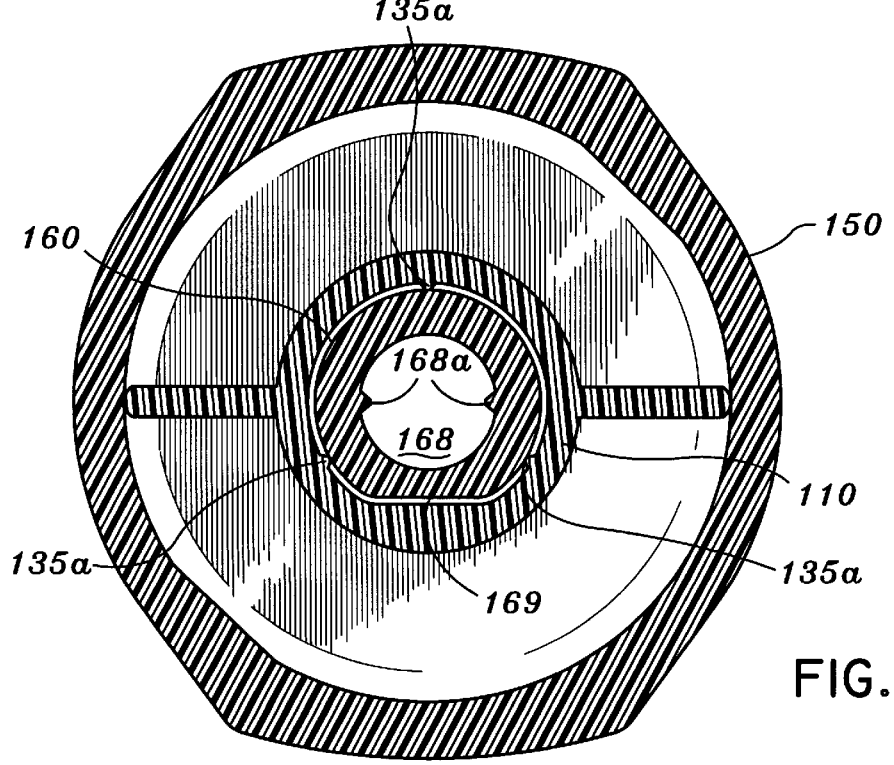
FIG. 17 is a sectional view of the disposable loading unit taken along line 17—17 in FIG. 16.

Referring now to FIGS. 16, and 17, the disposable loading unit 100 with suture anchor 10 mounted therein is shown in its initial configuration. The suture anchor 10 is held by collet 160, which is biased to its most proximal position relative to the housing 110 by means of spring 140. As can be seen from FIG. 17, the housing can include longitudinal ridges 135a spaced apart around the interior of bore 135. These ridges provide friction between the collet and the housing 110. Likewise, bore 168 can include ridges 168a to position outer tube 210 of the installation tool more precisely.

Figure 18:
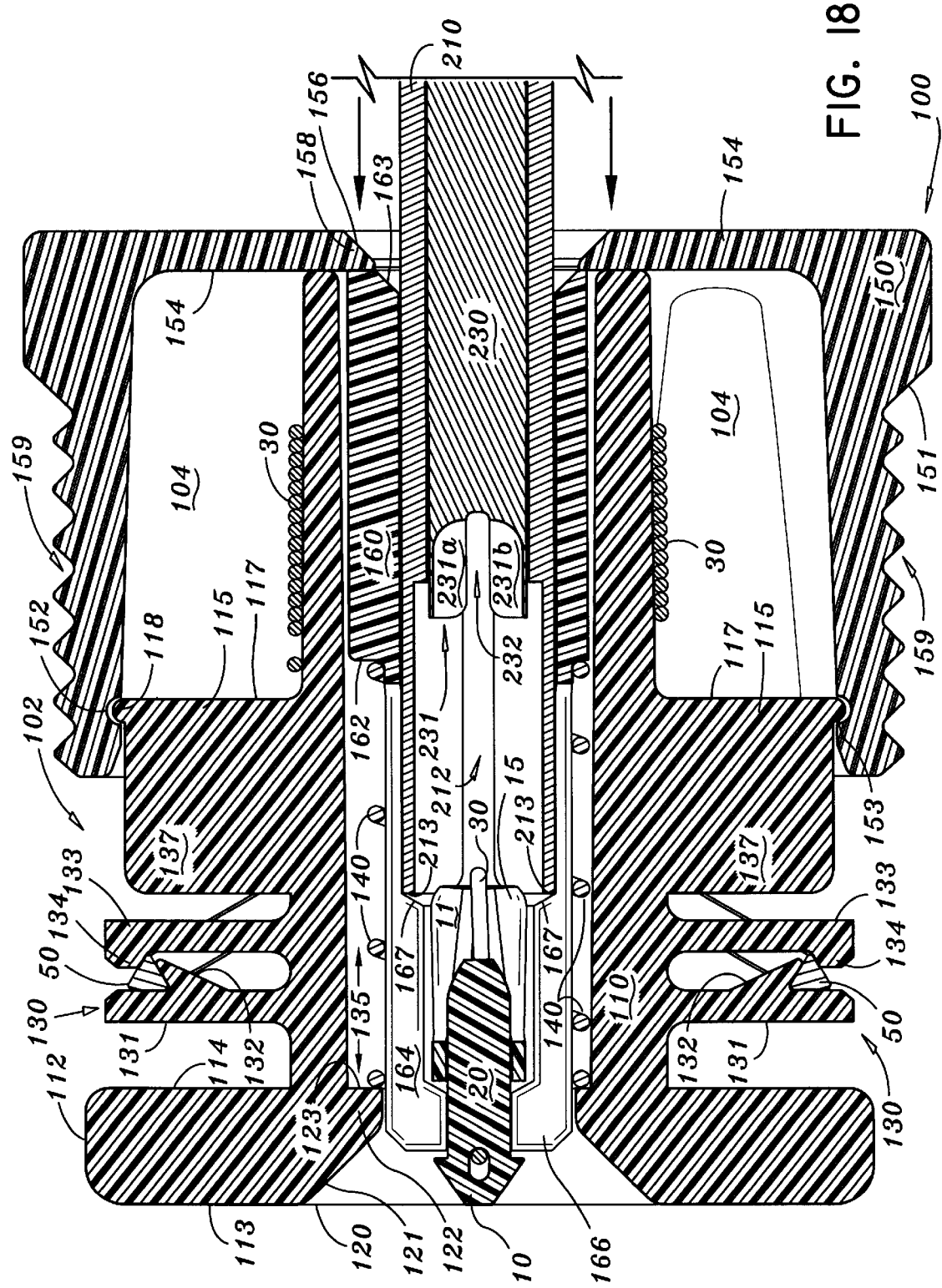
FIG. 18 is an enlarged side sectional view of the disposable loading unit showing advancement of the outer tube and inner shaft of the installation tool.
Figure 19:
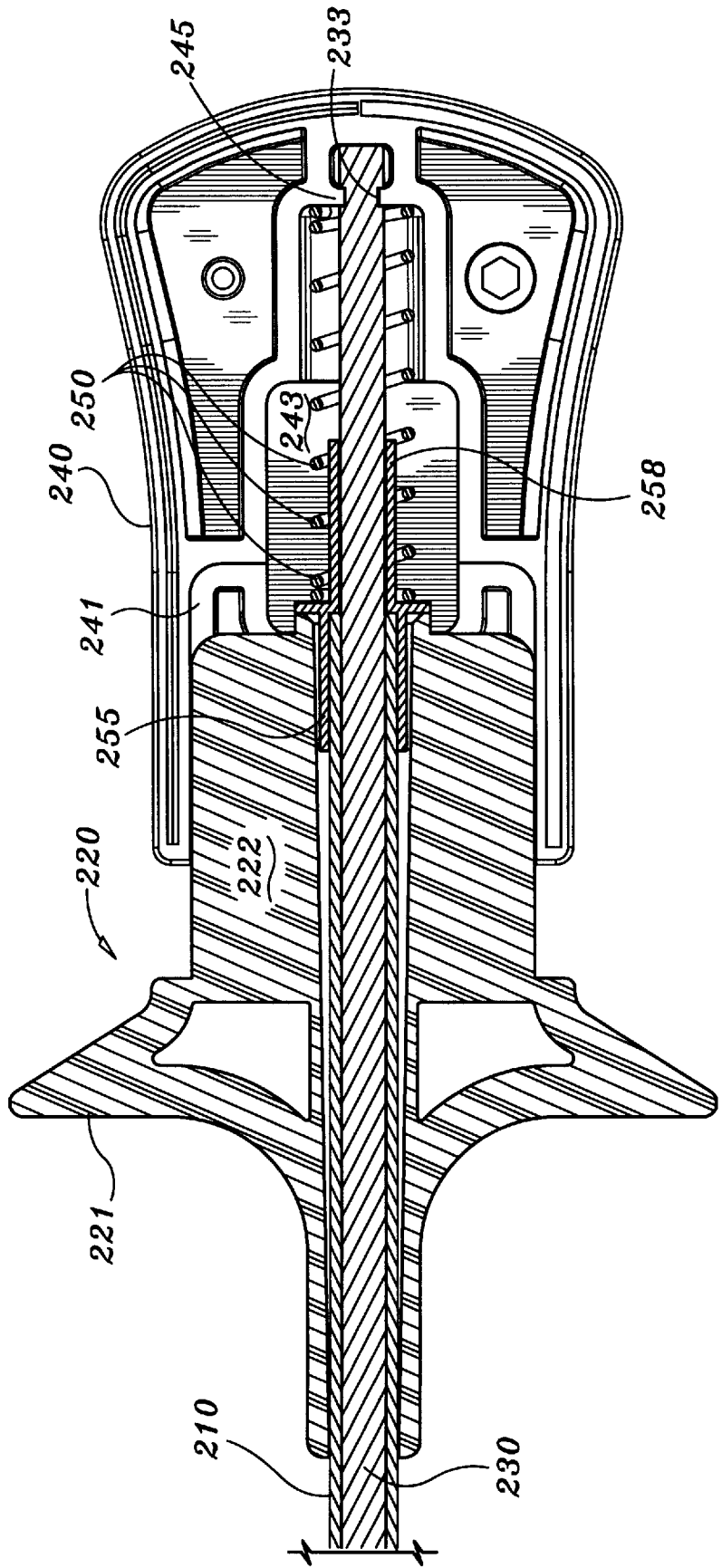
FIG. 19 is a sectional view of the handle portion of the installation tool.

Referring now to FIGS. 18 and 19, outer tube 210 is inserted through bore 135 of housing 110 until the distal edge 213 of the outer tube contacts camming surface 167 in the collet. The handle portion 202 of the installation tool is in the configuration illustrated in FIG. 19 at this stage of operation.

Figure 20:
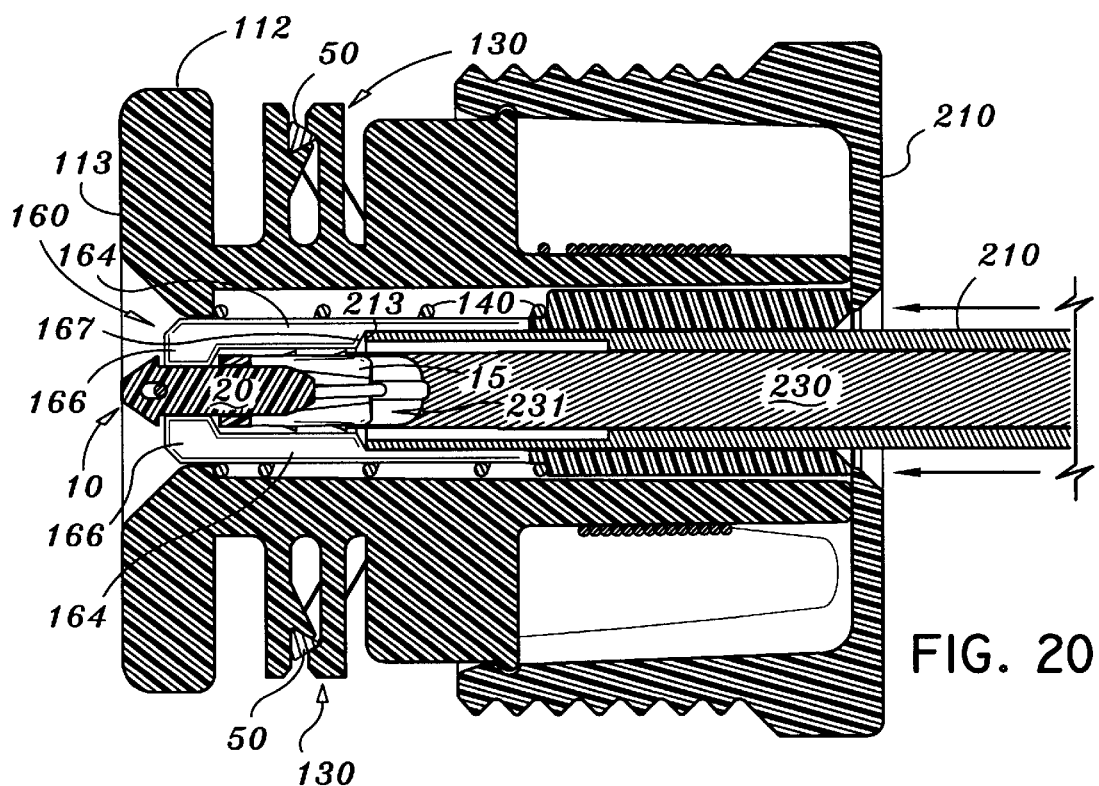
FIG. 20 is a sectional view of the disposable loading unit showing advancement of the outer tube and inner shaft of the installation tool.
Figure 21:
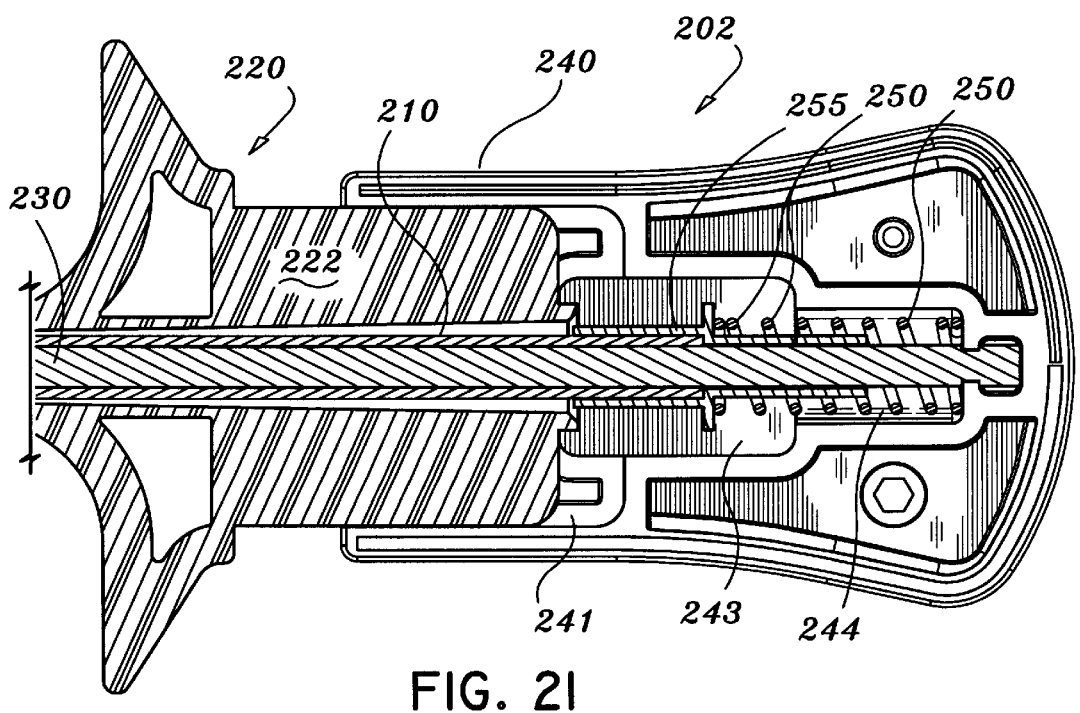
FIG. 21 is a sectional view of the handle portion of the installation tool.

Referring now to FIGS. 20 and 21, additional distal force is applied to the installation tool 200 by the surgeon, which advances the inner shaft 230 until the distal end opening 231 engages the proximal end portion of legs 15 of the suture anchor 10. The handle portion 202 of the installation tool is in the configuration illustrated in FIG. 21 at this stage. As one can see from FIG. 21, the outer tube 210 and connector 255 are pushed back in the proximal direction against the biasing force of spring 250, which compresses in response thereto.

Figure 22:
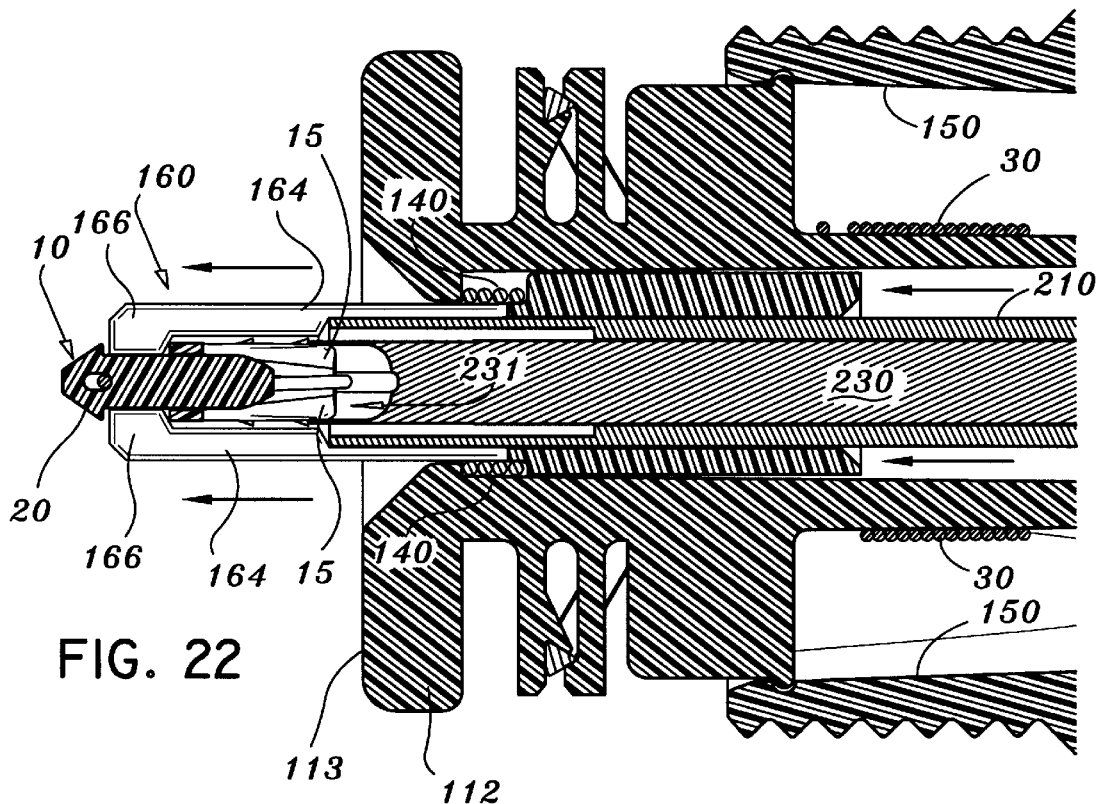
FIGS. 22, 23 and 24 are sectional side views showing advancement of the collet, release of the suture anchor by the collet, and advancement of the suture anchor by the installation tool.

Referring now to FIG. 22, further distal force applied by the surgeon moves the collet 160 out of the housing 110 against the biasing force of spring 140, which compresses.

Figure 23:
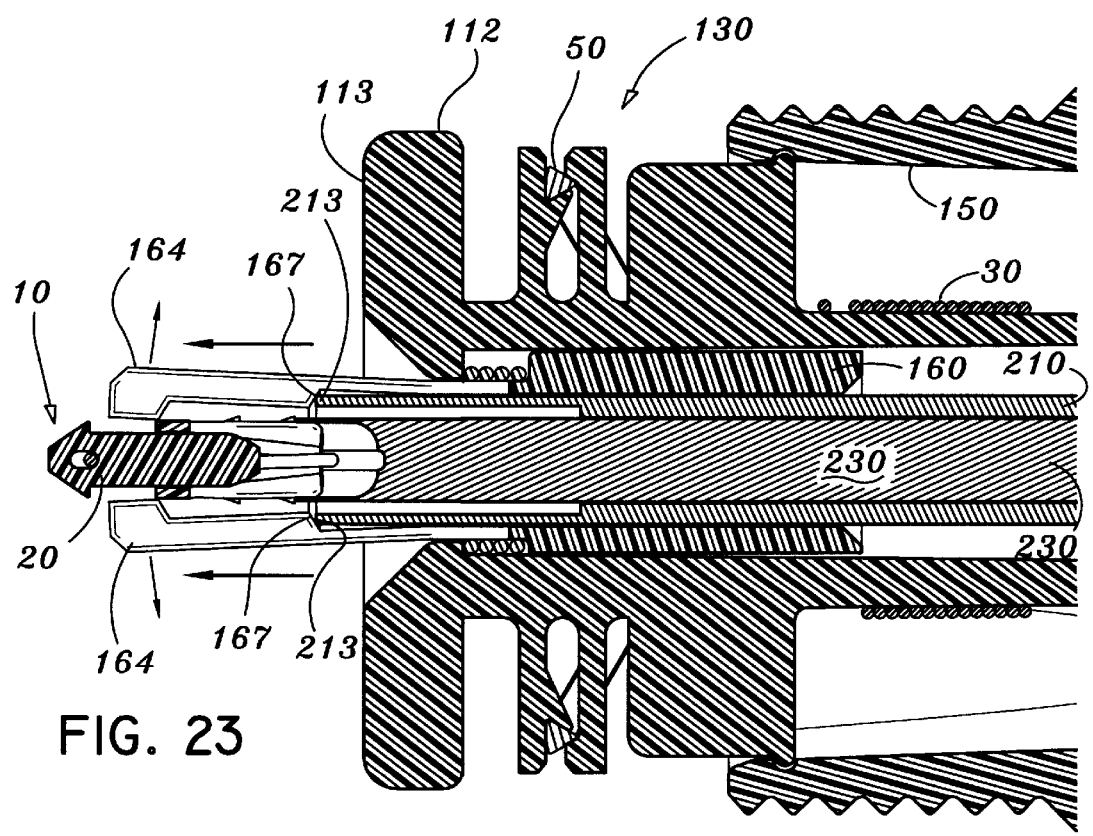

Referring now to FIG. 23, when spring 140 reaches full compression and the collet, 160 has reached its furthest distal extension beyond the distal extension beyond the distal surface 113 of flange 112, collet arms 164 are biased into an open configuration by the camming action of distal edge 213 on camming surface 167 as the outer tube continues to advance. Collet arms 164 release the suture anchor 10, which is held by the inner shaft 230.

Figure 24:
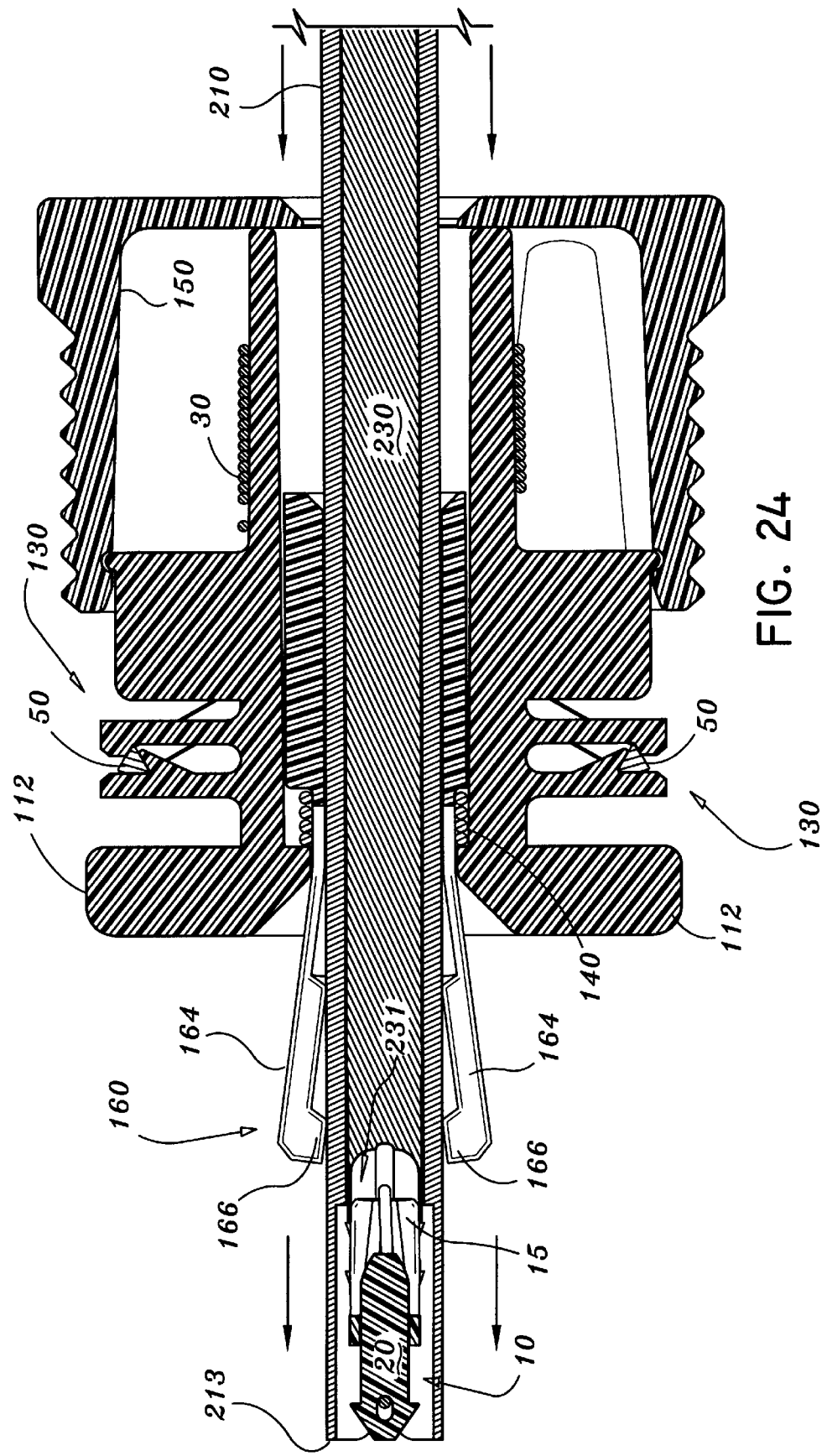

Referring now to FIGS. 24–26, once the outer tube 210 has pushed past the collet 160, it springs forward relative to the inner shaft 230 in response to the biasing action of spring 250, thereby at least partially enclosing the suture anchor 10. Suture 30 is positioned in notch 215 of the outer tube, while the proximal end of suture anchor 10 remains engaged within the distal opening 231 of inner shaft 230.

Figure 27:
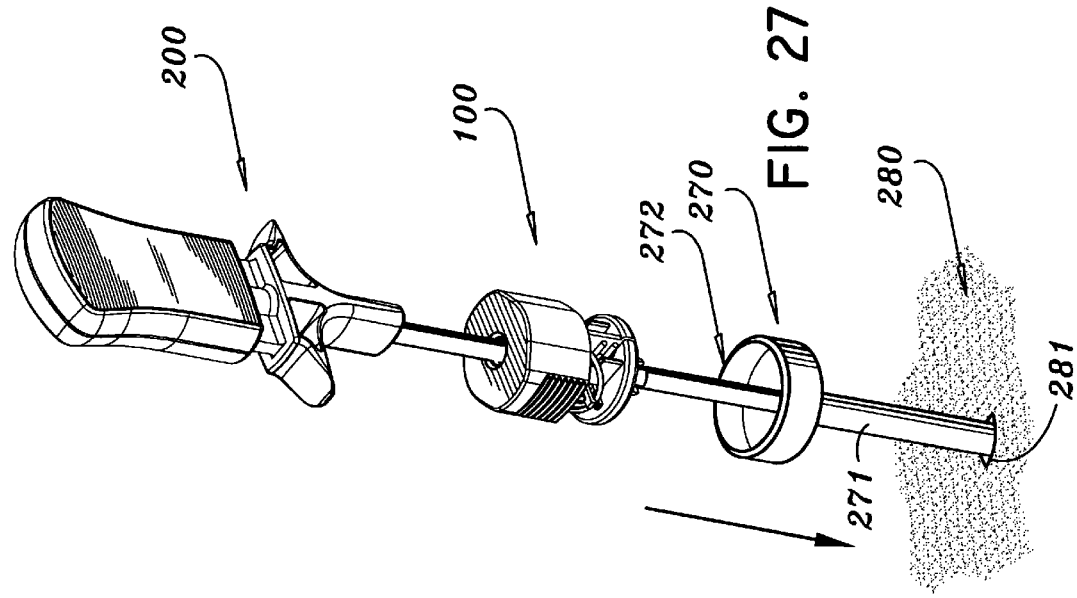

Referring now to FIG. 27, the installation tool 200 and loading unit 100 are shown in use in conjunction with a cannula 270 inserted through an opening 281 in body tissue 280. The cannula 270 includes a narrow endoscopic tube 271 and a non-endoscopic cap 272 to which the tube 271 is attached.

Figure 28:
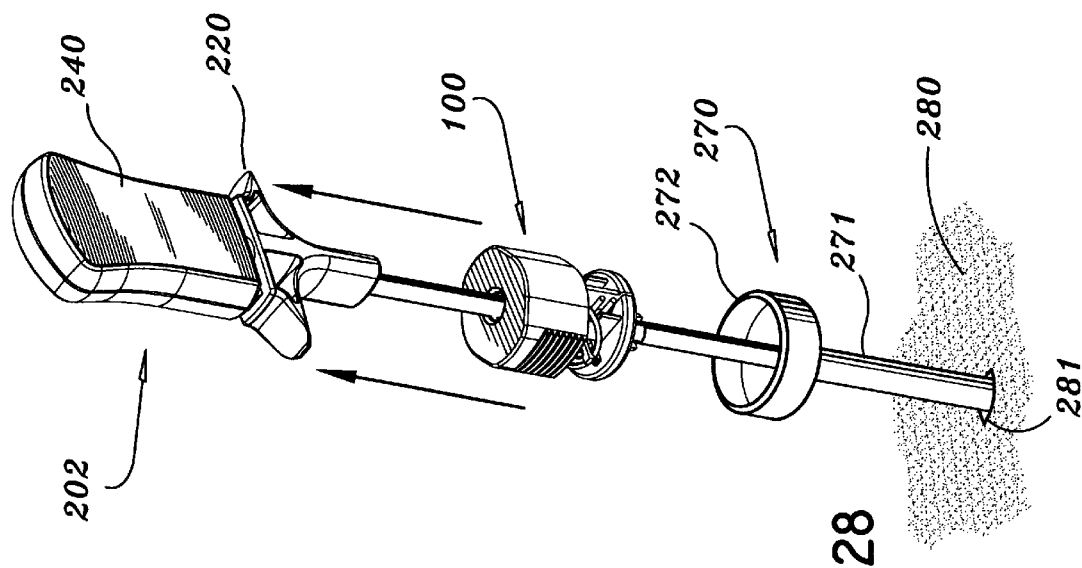
FIGS. 27 and 28 are perspective views illustrating the use of the suture anchor installation system.
Figure 29:
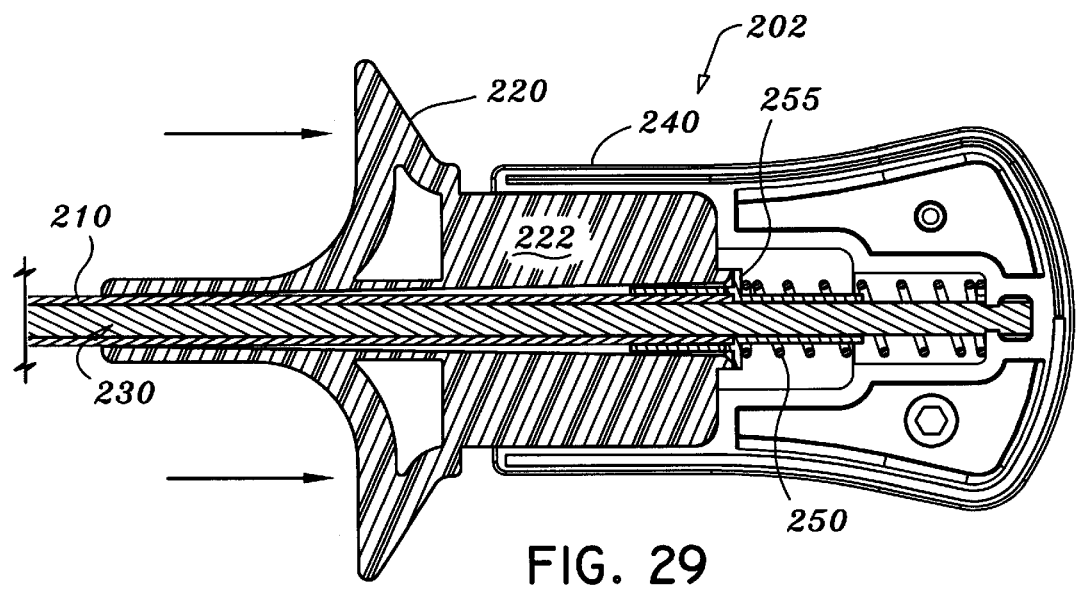
FIG. 29 is a sectional side view of the handle portion of the installation tool.
Figure 30:
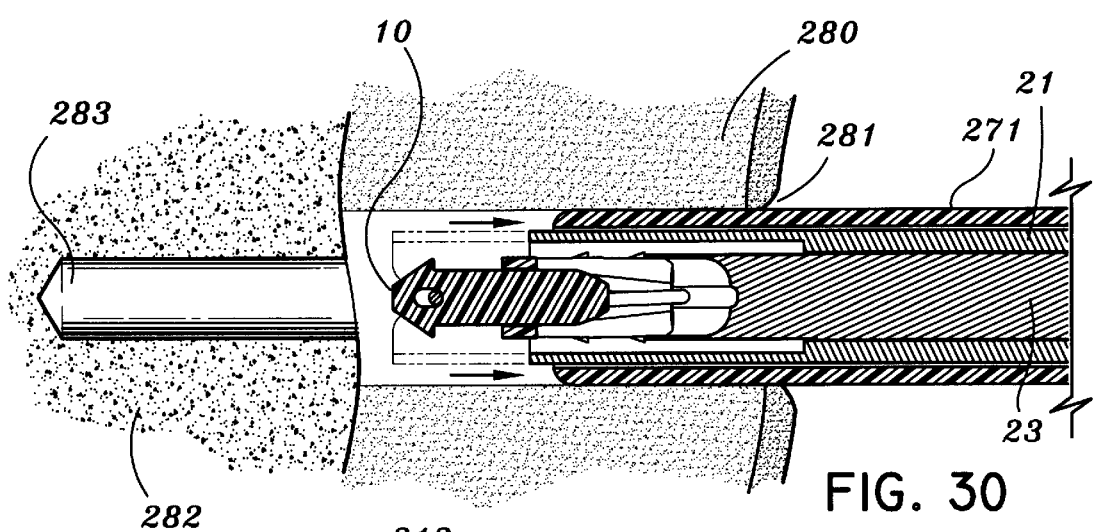
Figure 31:
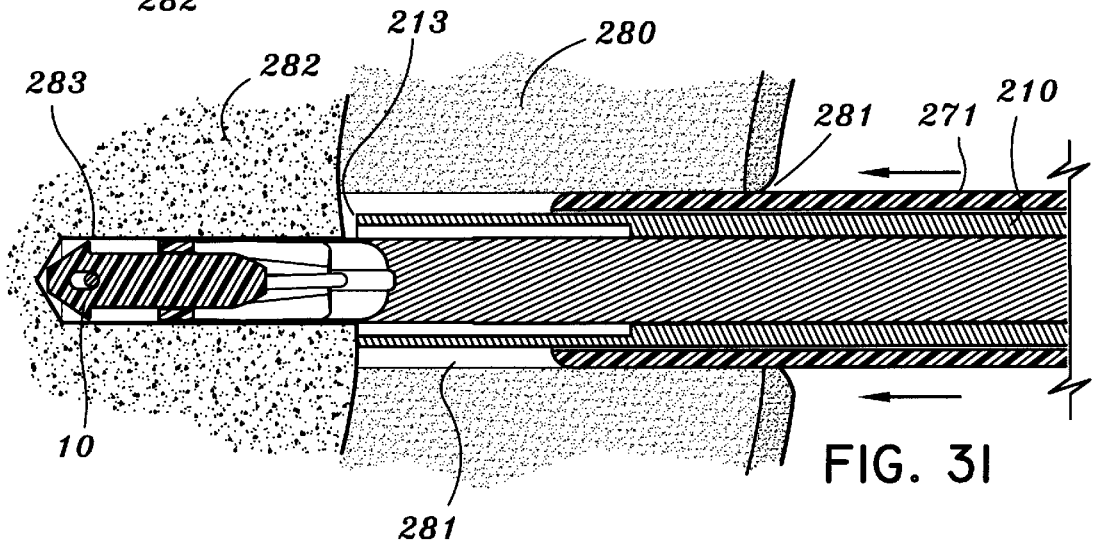

Referring to FIGS. 28–30, in accordance with a preferred method, an opening 281 is made in soft tissue 280 by creating an incision in the skin. Cannula tube 271 is inserted into the incision. Then, an obturator disposed through a drill guide (not shown) is deployed through the cannula tube 271 to create a soft tissue opening 281, thereby gaining access to the drilling site on the bone. The obturator is removed, and a drill bit inserted through the drill guide (not shown) is employed to drill an appropriately sized hole 283 in the bone 282. Next, the drill bit is removed and outer tube 210 is inserted through the drill guide, which remains disposed through cannula 270 and soft tissue opening 281. The outer tube 210 is positioned in alignment with hole 283 in bone mass 282. Trigger portion 220 of the installation tool is then pressed, which moves outer tube 210 proximally, while distal force applied to the handle advances the inner shaft 230 and suture anchor 10 toward the bone, thereby inserting the suture anchor 10 into hole 283 in the bone, as can be seen in FIG. 31. The handle permits partial retraction of outer tube 210 to permit the surgeon to visualize the suture anchor 10 prior to its insertion into the bone.

Referring to FIG. 32, the trigger portion 220 is released and the installation tool 200 is withdrawn from cannula 270 with suture 30 left extending through cannula tube 271.

Referring to FIG. 33, suture 30 is then pulled proximally to engage the setting pin 20 in socket 11. Referring also now to FIGS. 34 and 35, in the initial configuration of the suture anchor 10, setting pin 20 is extended distally from the socket 11, as seen in FIG. 34. Upon pulling the suture 30, however, setting pin 20 is pulled back into socket 11 and legs 15 are thereby radially expanded as shown in FIG. 36. This expansion of legs 15 locks the suture anchor 10 firmly into hole 283 in the bone 282.

Once the suture anchor 10 is securely installed the surgeon can remove the needles 50 and suture 30 from the disposable loading unit 100. Soft tissue 280 can be secured to the bone mass 282 by tying down the tissue with knots in the suture 30 in accordance with known surgical procedures.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

What is claimed is:

1. A suture installation system, comprising:
    a) a suture anchor which includes an elongated setting pin at least partially mounted within a longitudinal bore of a socket and slidably movable between a distal first position wherein at least a portion of the setting pin is distal to the socket and a proximal second position, the socket having at least two proximally pointing legs which are radially expandable in response to movement of the setting pin to the proximal second position;
    b) a loading unit for retaining the suture anchor, the loading unit including a housing and a collet for releasably gripping the suture anchor, the collet being movably mounted within an axial bore in the housing; and
    c) a suture anchor inserter having a first elongated member for engaging the collet, and a second elongated member for releasably engaging the socket.

2. The suture anchor installation system of claim 1 wherein each leg has at least one barb on an exterior surface thereof, and the setting pin has an aperture for reception therethrough of a suture.

3. The suture anchor installation system of claim 2 wherein the aperture is transverse to a longitudinal axis of the setting pin.

4. The suture anchor installation system of claim 2 wherein the suture anchor comprises a suture received through the aperture of the setting pin, and wherein a surgical needle is attached to at least one end of the suture.

5. The suture anchor installation system of claim 1 wherein the loading unit housing includes spaced apart distal and medial flanges, and at least one needle park positioned between the distal and medial flanges.

6. The suture anchor installation system of claim 5 wherein the needle park includes spaced apart first and second parallel resilient posts for releasably holding a surgical needle between the first and second posts in a snap-fit engagement.

7. The suture anchor installation system of claim 1 wherein the loading unit housing includes spaced apart distal and medial flanges.

8. The suture anchor installation system of claim 7 wherein the loading unit further comprises a cap which is releasably engageable with the housing.

9. The suture anchor installation system of claim 8 wherein the cap includes a back wall and a cylindrical barrel portion, the barrel portion being engageable with the medial flange of the housing to at least partially define an interior space.

10. The suture anchor installation system of claim 1 wherein the collet includes at least two arms for releasably holding the suture anchor.

11. The suture anchor installation system of claim 10 wherein the collet arms each include a camming surface.

12. The suture anchor installation system of claim 10 wherein the collet arms are radially expandable in response to the first elongated member contacting the camming surface with a force sufficient to move the collet arms.

13. The suture anchor installation system of claim 12 wherein the collet arms each have a distal portion for contacting the setting pin of the suture anchor distal to the socket.

14. The suture anchor installation system of claim 1 wherein the first elongated member is a tubular member having an axial bore and the second elongated member is slidably disposed within the bore of the first elongated member.

15. The suture anchor installation system of claim 14 wherein the first elongated member includes at least one slot extending longitudinally along an exterior surface of said member for reception therein of a length of suture.

16. A device for releasably holding a suture anchor, which comprises:
    a) a housing having a bore;
    b) a collet slidably disposed within the bore for supporting a suture anchor;
    c) a suture anchor mounted to the collet, the suture anchor having a suture connected thereto.

17. The device of claim 16 wherein the housing includes a chamber for storage of the suture.

18. The device of claim 16 wherein a needle is attached to each of two ends of the suture and the housing includes at least one needle part for releasably holding the needles.

19. The device of claim 16 further including a cap removably mounted to the housing, the cap at least partially defining an enclosed chamber for storage of the suture.

20. The device of claim 16 wherein the collet has at least two distally extending resilient arms for releasably gripping a suture anchor.

21. The device of claim 20 wherein each arm has a camming surface for receiving a distally directed force, the collet being movable from an initial position substantially completely within the bore of the housing to a second position wherein the at least two arms are positioned outside the bore of the housing in response to application of a distally directed force to the camming surface, and said at least two arms being movable from an initial position wherein the arms are substantially parallel to a second position wherein the arms are radially expanded in response to application of a sufficient magnitude of distally directed force to the camming surface after the arms of the collet have been moved outside the bore of the collet.

* * * * *